(12) United States Patent
Saito et al.

(10) Patent No.: US 8,999,442 B2
(45) Date of Patent: Apr. 7, 2015

(54) RUTHENIUM FILM-FORMING MATERIAL AND RUTHENIUM FILM-FORMING METHOD

(75) Inventors: Ryuichi Saito, Tokyo (JP); Kang-go Chung, Tokyo (JP); Hideki Nishimura, Tokyo (JP); Tatsuya Sakai, Tokyo (JP)

(73) Assignee: JSR Corporation, Tokyo (JP)

( * ) Notice: Subject to any disclaimer, the term of this patent is extended or adjusted under 35 U.S.C. 154(b) by 14 days.

(21) Appl. No.: 13/503,899

(22) PCT Filed: Oct. 20, 2010

(86) PCT No.: PCT/JP2010/068490
§ 371 (c)(1),
(2), (4) Date: Jul. 18, 2012

(87) PCT Pub. No.: WO2011/052453
PCT Pub. Date: May 5, 2011

(65) Prior Publication Data
US 2012/0282414 A1    Nov. 8, 2012

(30) Foreign Application Priority Data

Oct. 29, 2009  (JP) ................. 2009-248383
Apr. 23, 2010  (JP) ................. 2010-099416

(51) Int. Cl.
| | | |
|---|---|---|
| B05D 1/30 | (2006.01) | |
| B05D 1/02 | (2006.01) | |
| B05D 5/00 | (2006.01) | |
| B05D 7/00 | (2006.01) | |
| B28B 19/00 | (2006.01) | |
| B29B 15/10 | (2006.01) | |
| C23C 18/00 | (2006.01) | |
| C23C 20/00 | (2006.01) | |
| C23C 28/00 | (2006.01) | |
| C23C 16/18 | (2006.01) | |
| C07C 49/92 | (2006.01) | |
| C07F 15/00 | (2006.01) | |
| C23C 16/00 | (2006.01) | |
| H01L 21/768 | (2006.01) | |
| H01L 49/02 | (2006.01) | |

(52) U.S. Cl.
CPC .............. C23C 16/18 (2013.01); C07C 49/92 (2013.01); C07F 15/0046 (2013.01); H01L 21/76843 (2013.01); H01L 28/65 (2013.01)

(58) Field of Classification Search
CPC ........ C23C 16/00; C23C 15/18; C23C 18/00; C23C 18/12; C23C 18/1233; C23C 18/14
USPC ................... 427/255, 250, 248.1
See application file for complete search history.

(56) References Cited

U.S. PATENT DOCUMENTS

| | | | | |
|---|---|---|---|---|
| 6,316,064 | B1 * | 11/2001 | Onozawa et al. ............. | 427/585 |
| 2002/0055001 | A1 | 5/2002 | Funakubo et al. | |
| 2003/0068509 | A1 * | 4/2003 | Shah et al. ................... | 428/472 |
| 2003/0088116 | A1 * | 5/2003 | Kawano et al. .............. | 556/136 |
| 2003/0203112 | A1 | 10/2003 | Funakubo et al. | |
| 2003/0205168 | A1 | 11/2003 | Funakubo et al. | |
| 2005/0087135 | A1 | 4/2005 | Hioki et al. | |
| 2010/0055313 | A1 * | 3/2010 | Kadota et al. ............ | 427/255.28 |

FOREIGN PATENT DOCUMENTS

| | | |
|---|---|---|
| JP | 6-283438 | 10/1994 |
| JP | 11-35589 | 2/1999 |

(Continued)

OTHER PUBLICATIONS

Weinstein et al. Coating Flows, Annu Rev Fluid Mech 2004, 36, pp. 29-53.*

(Continued)

*Primary Examiner* — Kelly M Gambetta
(74) *Attorney, Agent, or Firm* — Oblon, McClelland, Maier & Neustadt, L.L.P.

(57) ABSTRACT

Disclosed is a ruthenium film-forming material having a lower melting point and a higher vapor pressure that facilitates supply of the material onto a base and moreover enables a high-quality ruthenium film to be obtained.

A ruthenium film-forming material includes a compound represented by general formula (1) below

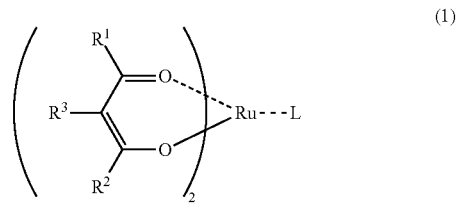

(1)

(wherein $R^1$ is independently at each occurrence a hydrogen atom, a halogen atom, a hydrocarbon group having 1 to 4 carbon atoms or a halogenated hydrocarbon group having 1 to 4 carbon atoms; $R^2$ is independently at each occurrence a halogenated hydrocarbon group having 1 to 4 carbon atoms, an alkoxy group having 1 to 4 carbon atoms or a halogenated alkoxy group having 1 to 4 carbon atoms, with the proviso that $R^1$ and $R^2$ are mutually differing groups; $R^3$ is independently at each occurrence a hydrogen atom or a hydrocarbon group having 1 to 4 carbon atoms; and L is an unsaturated hydrocarbon compound having 4 to 10 carbon atoms and having at least two double bonds).

11 Claims, No Drawings

(56) References Cited

FOREIGN PATENT DOCUMENTS

| JP | 2002-69639 | 3/2002 |
| JP | 2002-114795 | 4/2002 |
| JP | 2002-212112 | 7/2002 |
| JP | 2005-131632 | 5/2005 |
| JP | 2006-241557 | 9/2006 |
| JP | 2006241557 A * | 9/2006 |
| JP | 2008-124464 A | 5/2008 |
| JP | 2009-120916 | 6/2009 |
| JP | 2009120916 A * | 6/2009 |
| WO | WO 2008/013244 A1 | 1/2008 |

OTHER PUBLICATIONS

International Preliminary Report on Patentability and Written Opinion issued Jun. 12, 2012 in Application No. PCT/JP2010/068490.
International Search Report issued Jan. 25, 2011 in Application No. PCT/JP2010/068490.
Japanese Office Action issued Sep. 9, 2014 in Patent Application No. 2011-538370 (without EnglishTranslation).

* cited by examiner

RUTHENIUM FILM-FORMING MATERIAL AND RUTHENIUM FILM-FORMING METHOD

TECHNICAL FIELD

The present invention relates to a ruthenium film-forming material and a ruthenium film-forming method.

BACKGROUND ART

The increasing level of integration and miniaturization in semiconductor devices such as the dynamic random access memory (DRAM) has brought about a need to change the various metal film materials and metal oxide film materials making up the devices.

In particular, there is a desire for improvements in conductive metal films for multilevel metallization applications in semiconductor devices, and a changeover to high-conductivity copper interconnect lines is underway. To hold down interference between layers of such copper lines, low dielectric constant materials (i.e. low-k materials) are used as the interlayer dielectric material in multilevel metallization. However, one problem that has arisen is that oxygen atoms present within the low-k material are readily taken up by the copper lines, and lowers the conductivity of the lines. Hence, technology to form a barrier film between the low-k material and the copper lines is being studied for the purpose of preventing oxygen migration from the low-k material. Metallic ruthenium films are attracting attention as a material which does not readily take up oxygen from dielectric layers and which can easily be dry etched, and which are thus capable of being used as such barrier films. Metallic ruthenium is also noteworthy as materials capable of fulfilling at the same time both the role of the above-described barrier film and the role of a plating growth film in damascene film formation wherein the copper lines are buried by a plating process.

Moreover, in semiconductor device capacitors as well, on account of their high oxidation resistance and high conductivity, metallic ruthenium films have been attracting attention as electrode materials for high dielectric constant (i.e. high-k) materials such as alumina, tantalum pentoxide, hafnium oxide, and barium strontium titanate (BST).

Up until now, sputtering processes have commonly been used in the formation of such metallic ruthenium films. Recently, however, chemical vapor deposition is being studied as a way to achieve smaller structures, thinner films and greater amenability to mass production.

Yet, the metal films which are commonly formed in chemical vapor deposition, owing to the thin state of aggregation by microcrystals and other reasons, have a poor surface morphology. The use of compounds such as tris(dipivaloylmethanato)ruthenium, ruthenocene, bis(alkylcyclopentadienyl)ruthenium and (cyclohexadienyl)ruthenium tricarbonyl as chemical vapor deposition materials is currently being investigated as a means for solving such problems of morphology (see Patent Documents 1 to 4).

In addition, to prevent the degradation of materials adjoining the metallic ruthenium film during the film-forming step and stabilize the production conditions when the above-described chemical vapor deposition materials are used in a manufacturing operation, it is desired that the materials have a good storage stability. However, when existing compounds such as ruthenocene and bis(alkylcyclopentadienyl)ruthenium are used, the oxidation of adjoining materials and associated deterioration in performance arise in a short time due to the influence of oxygen admixture in the film-forming operation, as a result of which the resulting ruthenium film sometimes has a diminished conductivity. In the case of (cyclohexadienyl)ruthenium tricarbonyl, the film forming operation can be carried out in an inert atmosphere, but the ruthenium material itself sometimes has an inferior storage stability.

The use of bis(acetylacetonato)(1,5-cyclooctadiene)ruthenium as a chemical vapor deposition material has also been investigated (see Patent Document 5). Yet, this compound is a solid at an ordinary temperature and has a low vapor pressure. In order to reduce the design load of the vaporizer in the chemical vapor deposition apparatus, there has been a desire for a lower melting point and a higher vapor pressure.

BACKGROUND ART DOCUMENTS

Patent Documents

Patent Document 1: Japanese Patent Application Laid-open No. H6-283438
Patent Document 2: Japanese Patent Application Laid-open No. H11-35589
Patent Document 3: Japanese Patent Application Laid-open No. 2002-114795
Patent Document 4: Japanese Patent Application Laid-open No. 2002-212112
Patent Document 5: Japanese Patent Application Laid-open No. 2006-241557

DISCLOSURE OF THE INVENTION

Problems to be Solved by the Invention

It is therefore an object of the invention to provide a ruthenium film-forming material which has a lower melting point and a higher vapor pressure, and is easily supplied onto a base. Another object is to provide a ruthenium film-forming method which uses such a material.

Means for Solving the Problems

The inventors have conducted extensive investigations in order to achieve the above objects. As a result, they have discovered that the objects can be attained by using a compound of formula (1) below.

That is to say, the invention provides [1] to [8] below.

[1] A ruthenium film-forming material which includes a compound of formula (1) below

[Chem 1]

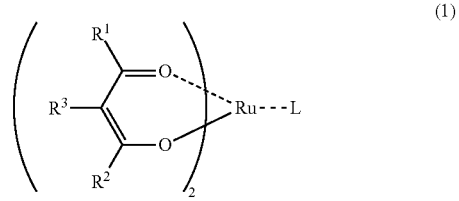

(wherein $R^1$ is independently at each occurrence a hydrogen atom, a halogen atom, a hydrocarbon group having 1 to 4 carbon atoms or a halogenated hydrocarbon group having 1 to 4 carbon atoms; $R^2$ is independently at each occurrence a halogenated hydrocarbon group having 1 to 4 carbon atoms, an alkoxy group having 1 to 4 carbon atoms or a halogenated alkoxy group having 1 to 4 carbon atoms, with the proviso that $R^1$ and $R^2$ are mutually differing groups; $R^3$ is independently at each occurrence a hydrogen atom or a hydrocarbon group having 1 to 4 carbon atoms; and L is an unsaturated hydrocarbon compound having 4 to 10 carbon atoms and having at least two double bonds).

[2] The ruthenium film-forming material according to [1] above, wherein in general formula (1), $R^1$ is a hydrocarbon group having 1 to 4 carbon atoms and $R^2$ is an alkoxy group having 1 to 4 carbon atoms.

[3] The ruthenium film-forming material according to [1] or [2] above, which is for use in chemical vapor deposition.

[4] A ruthenium film-forming method including using the ruthenium film-forming material according to any one of [1] to [3] above.

[5] A ruthenium film-forming method, including: a ruthenium film-forming material supply step of supplying the ruthenium film-forming material according to [3] above onto a base; and a film-forming step of forming a ruthenium film on the base by thermally decomposing the ruthenium film-forming material supplied onto the base.

[6] The ruthenium film-forming method according to [5] above, wherein thermal decomposition in the film-forming step is carried out at a temperature of from 100 to 800° C.

[7] The ruthenium film-forming method according to [5] or [6] above, wherein thermal decomposition in the film-forming step is carried out in an inert gas or a reducing gas.

[8] A ruthenium film-forming method, including: a film-forming step of coating the ruthenium film-forming material according to [1] or [2] above onto a base, and forming a ruthenium film on the base by subjecting the ruthenium film-forming material on the base to heat treatment and/or light treatment.

Effects of the Invention

The ruthenium film-forming material of the invention has a low melting point and a high vapor pressure, and therefore makes it easy to supply the material onto a base and enables a ruthenium film to be formed by a simple method.

The ruthenium film-forming material of the invention enables a high-purity and high-quality ruthenium film having a low level of residual impurities to be obtained.

EMBODIMENTS OF THE INVENTION

The invention is described more fully below.

The ruthenium film-forming material of the invention includes a compound represented by general formula (1) described below.

[Chem 2]

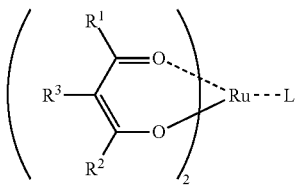

(1)

In general formula (1), $R^1$ is independently at each occurrence a hydrogen atom, a halogen atom, a hydrocarbon group having 1 to 4 carbon atoms or a halogenated hydrocarbon group having 1 to 4 carbon atoms; preferably a halogen atom, a hydrocarbon group having 1 to 4 carbon atoms or a halogenated hydrocarbon group having 1 to 4 carbon atoms; and more preferably, from the standpoint of thermal stability, a hydrocarbon group having 1 to 4 carbon atoms.

The halogen atom represented by $R^1$ is exemplified by a fluorine atom, a chlorine atom, a bromine atom and an iodine atom; preferably a fluorine atom or a chlorine atom; and more preferably a fluorine atom.

The hydrocarbon group having 1 to 4 carbon atoms represented by $R^1$ is exemplified by a methyl group, an ethyl group, an n-propyl group, an isopropyl group, an n-butyl group, an isobutyl group and a t-butyl group; and is preferably a methyl group, an ethyl group, an n-propyl group, an isopropyl group or a t-butyl group; and more preferably a methyl group or an ethyl group.

The halogenated hydrocarbon group having 1 to 4 carbon atoms represented by $R^1$ is preferably a fluorinated hydrocarbon group, a chlorinated hydrocarbon group or a brominated hydrocarbon group, and is more preferably a fluorinated hydrocarbon group.

Examples of the halogenated hydrocarbon group having 1 to 4 carbon atoms include a chloromethyl group, a dichloromethyl group, a trichloromethyl group, a fluoromethyl group, a difluoromethyl group, a trifluoromethyl group, a 2,2,2-trifluoroethyl group, a pentafluoroethyl group, a perfluoro-n-propyl group, a perfluoroisopropyl group, a perfluoro-n-butyl group, a perfluoroisobutyl group and a perfluoro-t-butyl group; preferred examples includes a fluoromethyl group, a difluoromethyl group, a trifluoromethyl group, a 2,2,2-trifluoroethyl group, a pentafluoroethyl group, a perfluoro-n-propyl group, a perfluoroisopropyl group and a perfluoro-t-butyl group; and more preferred examples include a fluoromethyl group, a difluoromethyl group, a trifluoromethyl group, a 2,2,2-trifluoroethyl group and a pentafluoroethyl group.

In general formula (1), $R^2$ is independently at each occurrence a halogenated hydrocarbon group having 1 to 4 carbon atoms, an alkoxy group having 1 to 4 carbon atoms or a halogenated alkoxy group having 1 to 4 carbon atoms; and preferably, from the standpoint of thermal stability, an alkoxy group having 1 to 4 carbon atoms.

Here, the halogenated hydrocarbon group having 1 to 4 carbon atoms represented by $R^2$ is exemplified by a chloromethyl group, a dichloromethyl group, a trichloromethyl group, a fluoromethyl group, a difluoromethyl group, a trifluoromethyl group, a 2,2,2-trifluoroethyl group, a pentafluoroethyl group, a perfluoro-n-propyl group, a perfluoroisopropyl group, a perfluoro-n-butyl group, a perfluoroisobutyl group and a perfluoro-t-butyl group; preferably a fluoromethyl group, a difluoromethyl group, a trifluoromethyl group, a 2,2,2-trifluoroethyl group, a pentafluoroethyl group, a perfluoro-n-propyl group, a perfluoroisopropyl group and a perfluoro-t-butyl group; and more preferably a fluoromethyl group, a difluoromethyl group, a trifluoromethyl group, a 2,2,2-trifluoroethyl group and a pentafluoroethyl group.

The alkoxy group having 1 to 4 carbon atoms represented by $R^2$ is exemplified by a methoxy group, an ethoxy group, an n-propoxy group, an isopropoxy group, an n-butoxy group, an isobutoxy group and a t-butoxy group; preferably a methoxy group, an ethoxy group, an n-propoxy group and an isopropoxy group; and more preferably a methoxy group and an ethoxy group.

The halogenated alkoxy group having 1 to 4 carbon atoms represented by $R^2$ is exemplified by a fluorinated alkoxy group, a chlorinated alkoxy group and a brominated alkoxy group. Among them, a fluorinated alkoxy group is preferred.

Examples of the halogenated alkoxy group having 1 to 4 carbon atoms include a chloromethoxy group, a dichloromethoxy group, a trichloromethoxy group, a fluoromethoxy group, a difluoromethoxy group, a trifluoromethoxy group, a 2,2,2-trifluoroethoxy group, a pentafluoroethoxy group, a perfluoro-n-propoxy group, a perfluoroisopropoxy group, a perfluoro-n-butoxy group, a perfluoroisobutoxy group and a perfluoro-t-butoxy group. Preferred examples include a fluoromethoxy group, a difluoromethoxy group, a trifluoromethoxy group, a 2,2,2-trifluoroethoxy group, a pentafluoroethoxy group, a perfluoro-n-propoxy group, a perfluoroisopropoxy group and a perfluoro-t-butoxy group. More preferred examples include a fluoromethoxy group, a difluoromethoxy group, a trifluoromethoxy group, a 2,2,2-trifluoroethoxy group and a pentafluoroethoxy group.

In general formula (1), $R^3$ is independently at each occurrence a hydrogen atom or a hydrocarbon group having 1 to 4 carbon atoms, and is preferably a hydrogen atom.

In the invention, $R^1$ and $R^2$ in general formula (1) are mutually differing groups.

By having $R^1$ and $R^2$ in general formula (1) be differing groups, the melting point of the compound of general formula (1) can be lowered and the vapor pressure can be increased. As a result, the ruthenium film-forming material is more easily supplied onto a base, making it possible to form the ruthenium film by a simple method. The compound represented by general formula (1) is preferably a liquid at ordinary temperature (25° C.) and ordinary pressure (1 atm).

By having $R^1$ and $R^2$ be a combination of a hydrocarbon group and an alkoxy group, a compound having an excellent thermal stability and having in particular an excellent storage stability at high temperatures can be obtained.

In general formula (1), L is an unsaturated hydrocarbon compound having 4 to 10 carbon atoms and having at least two double bonds.

Examples of L in general formula (1) include acyclic dienes such as 1,3-pentadiene, 1,5-hexadiene, 1,4-hexadiene, 1,3-hexadiene, 2,4-hexadiene, 3-methyl-1,3-pentadiene, 2-methyl-1,4-pentadiene, 1,6-heptadiene, 1,5-heptadiene, 1,4-heptadiene, 1,7-octadiene, 1,6-octadiene, 1,5-octadiene, 1,4-octadiene, 1,8-nonadiene, 1,7-nonadiene, 1,6-nonadiene, 1,5-nonadiene, 1,4-nonadiene, 1,3-nonadiene, 1,9-decadiene, 1,8-decadiene, 1,7-decadiene, 1,6-decadiene, 1,5-decadiene, 1,4-decadiene and 1,3-decadiene; and cyclic dienes such as 1,5-cyclooctadiene, 1,3-cyclooctadiene, 1,4-cyclohexadiene and 1,3-cyclohexadiene.

An example of the method of synthesizing the compound represented by formula (1) includes the steps of: (a) reacting ruthenium trichloride with the unsaturated hydrocarbon compound having 4 to 10 carbon atoms and having at least two double bonds denoted by L in general formula (1) to form a compound represented by of formula (2) described below, and (b) reacting the compound represented by formula (2) with the compound represented by formula (3) described below.

[Chem 3]

(2)

[Chem 4]

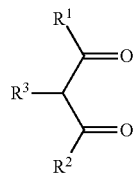

(3)

In above-described Step (a), the molar ratio in the reaction of ruthenium trichloride with the unsaturated hydrocarbon compound having 4 to 10 carbon atoms and having at least two double bonds denoted by L in general formula (1) (i.e. unsaturated hydrocarbon compound having 4 to 10 carbon atoms and having at least two double bonds denoted by L in general formula (1)/ruthenium trichloride) is preferably from 1 to 50, and more preferably from 2 to 20.

The temperature when carrying out the reaction varies also depending on the type of solvent, but generally is from 40 to 180° C., preferably from 60 to 140° C., and more preferably from 80 to 100° C. The reaction time is generally from 0.5 to 48 hours, preferably from 1 to 24 hours, and more preferably from 2 to 10 hours.

In above-described Step (b), the molar ratio in the reaction of the compound represented by general formula (2) with the compound represented by general formula (3) (i.e. compound of general formula (3)/compound of general formula (2)) is preferably from 2 to 10, and more preferably from 2.2 to 4.

The temperature when carrying out the reaction varies also depending on the type of solvent, but is generally from 40 to 180° C., preferably from 60 to 140° C., and more preferably from 80 to 100° C. The reaction time is generally from 0.5 to 48 hours, preferably from 1 to 24 hours, and more preferably from 2 to 10 hours.

From the standpoint of reactivity and solubility, it is preferable for the solvents used in the reactions in Steps (a) and (b) to be water, alcohols, ketones, ethers, esters, nitriles or halogenated hydrocarbons. Examples of the solvents include alcohols such as methanol, ethanol, n-propanol, isopropanol and butanol; ketones such as acetone, methyl ethyl ketone, diethyl ketone, dibutyl ketone and t-butyl methyl ketone; ethers such as dimethyl ether, diethyl ether, dibutyl ether, tetrahydrofuran and dioxane; esters such as ethyl acetate and butyl acetate; nitriles such as acetonitrile and propionitrile; and halogenated hydrocarbons such as methylene chloride, chloroform, tetrachloroethane, phenyl chloride and phenyl bromide.

Among the above solvents, ethanol, n-propanol and isopropanol are more preferred. A combination of two or more of the above solvents may also be used as the solvent in the reactions.

The reactions are preferably carried out in a thoroughly dried inert gas atmosphere. Examples of the inert gas include nitrogen, helium and argon.

Examples of the compound represented by formula (1) include the following.

Examples of compounds in which $R^1$ is a hydrogen atom and $R^2$ is a halogenated hydrocarbon group having 1 to 4 carbon atoms include bis(4,4,4-trifluoro-1,3-butanedionato)(η-1,6-heptadiene)ruthenium(II), bis(4,4,5,5,5-pentafluoro-1,3-pentanedionato)(η-1,6-heptadiene)ruthenium(II), bis(4,4,5,5,6,6,6-heptafluoro-1,3-hexanedionato)(η-1,6-heptadiene)ruthenium(II), bis(4,4,5,5,6,6,7,7,7-nonafluoro-1,3-heptanedionato)(η-1,6-heptadiene)ruthenium(II), bis(4,4,4-trifluoro-1,3-butanedionato)(η-1,7-octadiene)ruthenium(II), bis(4,4,5,5,5-pentafluoro-1,3-pentanedionato)(η-1,7-octadiene)ruthenium(II), bis(4,4,4-trifluoro-1,3-butanedionato)(η-1,4-cyclohexadiene)ruthenium(II), bis(4,4,5,5,5-pentafluoro-1,3-pentanedionato)(η-1,4-cyclohexadiene)ruthenium(II), bis(4,4,4-trifluoro-1,3-butanedionato)(η-1,5-cyclooctadiene)ruthenium(II), bis(4,4,5,5,5-pentafluoro-1,3-pentanedionato)(η-1,5-cyclooctadiene)ruthenium(II) and bis(4,4,5,5,6,6,6-heptafluoro-2,4-hexanedionato)(η-1,5-cyclooctadiene)ruthenium(II).

Examples of compounds in which $R^1$ is a hydrogen atom and $R^2$ is an alkoxy group having 1 to 4 carbon atoms include bis(methyl-3-oxopropionato)(η-1,6-heptadiene)ruthenium(II), bis(ethyl-3-oxopropionato)(η-1,6-heptadiene)ruthenium(II), bis(n-propyl-3-oxopropionato)(η-1,6-heptadiene)ruthenium(II), bis(isopropyl-3-oxopropionato)(η-1,6-heptadiene)ruthenium(II), bis(t-butyl-3-oxopropionato)(η-1,6-heptadiene)ruthenium(II), bis(methyl-3-oxopropionato)(η-1,4-cyclohexadiene)ruthenium(II), bis(ethyl-3-oxopropionato)(η-1,4-cyclohexadiene)ruthenium(II), bis(n-propyl-3-oxopropionato)(η-1,4-cyclohexadiene)ruthenium(II), bis(isopropyl-3-oxopropionato)(η-1,4-cyclohexadiene)ruthenium(II), bis(t-butyl-3-oxopropionato)(η-1,4-cyclohexadiene)ruthenium(II), bis(methyl-3-oxopropionato)(η-1,5-cyclooctadiene)ruthenium(II), bis(ethyl-3-oxopropionato)(η-1,5-cyclooctadiene)ruthenium(II), bis(n-propyl-3-oxopropionato)(η-1,5-cyclooctadiene)ruthenium(II), bis(isopropyl-3-oxopropionato)(η-1,5-cyclooctadiene)ruthenium(II) and bis(t-butyl-3-oxopropionato)(η-1,5-cyclooctadiene)ruthenium(II).

Examples of compounds in which $R^1$ is a hydrogen atom and $R^2$ is a halogenated alkoxy group having 1 to 4 carbon atoms include bis(trifluoromethyl-3-oxopropionato)(η-1,6-heptadiene)ruthenium(II), bis(pentafluoroethyl-3-oxopropionato)(η-1,6-heptadiene)ruthenium(II), bis(perfluoro-n-propyl-3-oxopropionato)(η-1,6-heptadiene)ruthenium(II), bis(perfluoroisopropyl-3-oxopropionato)(η-1,6-heptadiene)ruthenium(II), bis(perfluoro-t-butyl-3-oxopropionato)(η-1,6-heptadiene)ruthenium(II), bis(trifluoromethyl-3-oxopropionato)(η-1,4-cyclohexadiene)ruthenium(II), bis(pentafluoroethyl-3-oxopropionato)(η-1,4-cyclohexadiene)ruthenium(II), bis(perfluoro-n-propyl-3-oxopropionato)(η-1,4-cyclohexadiene)ruthenium(II), bis(perfluoroisopropyl-3-oxopropionato)(η-1,4-cyclohexadiene)ruthenium(II), bis(perfluoro-t-butyl-3-oxopropionato)(η-1,4-cyclohexadiene)ruthenium(II), bis(trifluoromethyl-3-oxopropionato)(η-1,5-cyclooctadiene)ruthenium(II), bis(pentafluoroethyl-3-oxopropionato)(η-1,5-cyclooctadiene)ruthenium(II), bis(perfluoro-n-propyl-3-oxopropionato)(η-1,5-cyclooctadiene)ruthenium(II), bis(perfluoroisopropyl-3-oxopropionato)(η-1,5-cyclooctadiene)ruthenium(II) and bis(perfluoro-t-butyl-3-oxopropionato)(η-1,5-cyclooctadiene)ruthenium(II).

Examples of compounds in which $R^1$ is a halogen atom and $R^2$ is a halogenated hydrocarbon group having 1 to 4 carbon atoms include bis(1,4,4,4-tetrafluoro-1,3-butanedionato)(η-1,6-heptadiene)ruthenium(II), bis(1,4,4,5,5,5-hexafluoro-1,3-pentanedionato)(η-1,6-heptadiene)ruthenium(II), bis(1,4,4,4-tetrafluoro-1,3-butanedionato)(η-1,7-octadiene)ruthenium(II), bis(1,4,4,5,5,5-hexafluoro-1,3-pentanedionato)(η-1,7-octadiene)ruthenium(II), bis(1,4,4,4-tetrafluoro-1,3-butanedionato)(η-1,4-cyclohexadiene)ruthenium(II), bis(1,4,4,5,5,5-hexafluoro-1,3-pentanedionato)(η-1,4-cyclohexadiene)ruthenium(II), bis(1,4,4,4-tetrafluoro-1,3-butanedionato)(η-1,5-cyclooctadiene)ruthenium(II), bis(1,4,4,5,5,5-hexafluoro-1,3-pentanedionato)(η-1,5-cyclooctadiene)ruthenium(II), bis(1,1,1,5,5,5-hexafluoro-2,4-pentanedionato)(η-1,5-cyclooctadiene)ruthenium(II) and bis(1,1,1,5,5,6,6,6-octafluoro-2,4-hexanedionato)(η-1,5-cyclooctadiene)ruthenium(II).

Examples of compounds in which $R^1$ is a halogen atom and $R^2$ is an alkoxy group having 1 to 4 carbon atoms include bis(methyl-3-fluoro-3-oxopropionato)(η-1,6-heptadiene)ruthenium(II), bis(ethyl-3-fluoro-3-oxopropionato)(η-1,6-heptadiene)ruthenium(II), bis(n-propyl-3-fluoro-3-oxopropionato)(η-1,6-heptadiene)ruthenium(II), bis(isopropyl-3-fluoro-3-oxopropionato)(η-1,6-heptadiene)ruthenium(II), bis(t-butyl-3-fluoro-3-oxopropionato)(η-1,6-heptadiene)ruthenium(II), bis(methyl-3-fluoro-3-oxopropionato)(η-1,4-cyclohexadiene)ruthenium(II), bis(ethyl-3-fluoro-3-oxopropionato)(η-1,4-cyclohexadiene)ruthenium(II), bis(n-propyl-3-fluoro-3-oxopropionato)(1,4-cyclohexadiene)ruthenium(II), bis(isopropyl-3-fluoro-3-oxopropionato)(η-1,4-cyclohexadiene)ruthenium(II), bis(t-butyl-3-fluoro-3-oxopropionato)(n-1,4-cyclohexadiene)ruthenium(II), bis(methyl-3-fluoro-3-oxopropionato)(η-1,5-cyclooctadiene)ruthenium(II), bis(ethyl-3-fluoro-3-oxopropionato)(η-1,5-cyclooctadiene)ruthenium(II), bis(n-propyl-3-fluoro-3-oxopropionato)(η-1,5-cyclooctadiene)ruthenium(II), bis(isopropyl-3-fluoro-3-oxopropionato)(η-1,5-cyclooctadiene)ruthenium(II) and bis(t-butyl-3-fluoro-3-oxopropionato)(η-1,5-cyclooctadiene)ruthenium(II).

Examples of compounds in which $R^1$ is a halogen atom and $R^2$ is a halogenated alkoxy group having 1 to 4 carbon atoms include bis(trifluoromethyl-3-fluoro-3-oxopropionato)(η-1,6-heptadiene)ruthenium(II), bis(pentafluoroethyl-3-fluoro-3-oxopropionato)(η-1,6-heptadiene)ruthenium(II), bis(perfluoro-n-propyl-3-fluoro-3-oxopropionato)(η-1,6-heptadiene)ruthenium(II), bis(perfluoroisopropyl-3-fluoro-3-oxopropionato)(η-1,6-heptadiene)ruthenium(II), bis(perfluoro-t-butyl-3-fluoro-3-oxopropionato)(η-1,6-heptadiene)ruthenium(II), bis(trifluoromethyl-3-fluoro-3-oxopropionato)(η-1,4-cyclohexadiene)ruthenium(II), bis(pentafluoroethyl-3-fluoro-3-oxopropionato)(η-1,4-cyclohexadiene)ruthenium(II), bis(perfluoro-n-propyl-3-fluoro-3-oxopropionato)(1,4-cyclohexadiene)ruthenium(II), bis(perfluoroisopropyl-3-fluoro-3-oxopropionato)(η-1,4-cyclohexadiene)ruthenium(II), bis(perfluoro-t-butyl-3-fluoro-3-oxopropionato)(η-1,4-cyclohexadiene)ruthenium(II), bis(trifluoromethyl-3-fluoro-3-oxopropionato)(η-1,5-cyclooctadiene)ruthenium(II), bis(pentafluoroethyl-3-fluoro-3-oxopropionato)(η-1,5-cyclooctadiene)ruthenium(II), bis(perfluoro-n-propyl-3-fluoro-3-oxopropionato)(1,5-cyclooctadiene)ruthenium(II), bis(perfluoroisopropyl-3-fluoro-3-oxopropionato)(η-1,5-cyclooctadiene)ruthenium(II) and bis(perfluoro-t-butyl-3-fluoro-3-oxopropionato)(η-1,5-cyclooctadiene)ruthenium(II).

Examples of compounds in which $R^1$ is a hydrocarbon group having 1 to 4 carbon atoms and $R^2$ is a halogenated hydrocarbon group having 1 to 4 carbon atoms include bis(1,1,1-trifluoro-2,4-pentanedionato)(η-1,6-heptadiene)ruthenium(II), bis(5,5,6,6,6-pentafluoro-2,4-hexanedionato)(η-1,6-heptadiene)ruthenium(II), bis(1,1,1-trifluoro-2,4-hexanedionato)(η-1,6-heptadiene)ruthenium(II), bis(1,1,1,2,2-pentafluoro-3,5-heptanedionato)(η-1,6-heptadiene)ruthenium(II), bis(1,1,1-trifluoro-2,4-pentanedionato)(η-1,7-octadiene)ruthenium(II), bis(5,5,6,6,6-pentafluoro-2,4-pentanedionato)(η-1,7-octadiene)ruthenium(II), bis(1,1,1-trifluoro-2,4-hexanedionato)(η-1,7-octadiene)ruthenium(II), bis(1,1,1,2,2-pentafluoro-3,5-heptanedionato)octadiene)ruthenium(II), bis(1,1,1-trifluoro-2,4-pentanedionato)(η-1,4-cyclohexadiene)ruthenium(II), bis(5,5,6,6,6-pentafluoro-2,4-pentanedionato)(η-1,4-cyclohexadiene)ruthenium(II), bis(1,1,1-trifluoro-2,4-hexanedionato)(η-1,4-cyclohexadiene)ruthenium(II), bis(1,1,1,2,2-pentafluoro-3,5-heptanedionato)(η-1,4-cyclohexadiene)ruthenium(II), bis(1,1,1,5,5,5-hexafluoro-2,4-pentanedionato)(η-1,4-cyclohexadiene)ruthenium(II), bis(1,1,1,5,5,6,6,6-octafluoro-2,4-hexanedionato)(η-1,4-cyclohexadiene)ruthenium(II), bis(1,1,1,2,2,6,6,7,7,7-decafluoro-3,5-pentanedionato)(η-1,4-cyclohexadiene)ruthenium(II), bis(1,1,1-trifluoro-2,4-pentanedionato)(η-1,5-cyclooctadiene)ruthenium(II), bis(5,5,6,6,6-pentafluoro-2,4- pentanedionato)(η-1,5-cyclooctadiene)ruthenium(II), bis(1,1,1-trifluoro-2,4-hexanedionato)(η-1,5-cyclooctadiene) ruthenium(II), bis(1,1,1,2,2-pentafluoro-3,5-heptanedionato)(η-1,5-cyclooctadiene)ruthenium(II) and bis (1,1,1,2,2,6,6,7,7,7-decafluoro-3,5-pentanedionato)(η-1,5-cyclooctadiene)ruthenium(II).

Examples of compounds in which $R^1$ is a hydrocarbon group having 1 to 4 carbon atoms and $R^2$ is an alkoxy group having 1 to 4 carbon atoms include bis(methyl-3-oxobutanato)(η-1,6-heptadiene)ruthenium(II), bis(ethyl-3-oxobutanato)(η-1,6-heptadiene)ruthenium(II), bis(n-propyl-3-oxobutanato)(η-1,6-heptadiene)ruthenium(II), bis(isopropyl-3-oxobutanato)(η-1,6-heptadiene)ruthenium(II), bis(n-butyl-3-oxobutanato)(η-1,6-heptadiene)ruthenium(II), bis(t-butyl-3-oxobutanato)(η-1,6-heptadiene)ruthenium(II), bis(methyl-3-oxobutanato)(η-1,7-octadiene)ruthenium(II), bis(ethyl-3-oxobutanato)(η-1,7-octadiene)ruthenium(II), bis(n-propyl-3-oxobutanato)(η-1,7-octadiene)ruthenium(II), bis(isopropyl-3-oxobutanato)(η-1,7-octadiene)ruthenium(II), bis(n-butyl-3-oxobutanato)(η-1,7-octadiene)ruthenium(II), bis(t-butyl-3-oxobutanato)(η-1,7-octadiene)ruthenium(II), bis(methyl-3-oxobutanato)(η-1,4-cyclohexadiene)ruthenium(II), bis(ethyl-3-oxobutanato)(η-1,4-cyclohexadiene)ruthenium(II), bis(n-propyl-3-oxobutanato)(η-1,4-cyclohexadiene)ruthenium(II), bis(isopropyl-3-oxobutanato)(η-1,4-cyclohexadiene)ruthenium(II), bis(n-butyl-3-oxobutanato)(η-1,4-cyclohexadiene)ruthenium(II), bis(t-butyl-3-oxobutanato)(η-1,4-cyclohexadiene)ruthenium(II), bis(methyl-3-oxopropanato)(η-1,4-cyclohexadiene)ruthenium(II), bis(ethyl-3-oxopropanato)(η-1,4-cyclohexadiene)ruthenium(II), bis(n-propyl-3-oxopropanato)(η-1,4-cyclohexadiene)ruthenium(II), bis(isopropyl-3-oxopropanato)(η-1,4-cyclohexadiene)ruthenium(II), bis(n-butyl-3-oxopropanato)(η-1,4-cyclohexadiene)ruthenium(II), bis(t-butyl-3-oxopropanato)(η-1,4-cyclohexadiene)ruthenium(II), bis(methyl-3-oxobutanato)(η-1,5-cyclooctadiene)ruthenium(II), bis(ethyl-3-oxobutanato)(η-1,5-cyclooctadiene)ruthenium(II), bis(n-propyl-3-oxobutanato)(η-1,5-cyclooctadiene)ruthenium(II), bis(isopropyl-3-oxobutanato)(η-1,5-cyclooctadiene)ruthenium(II), bis(n-butyl-3-oxobutanato)(η-1,5-cyclooctadiene)ruthenium(II), bis(t-butyl-3-oxobutanato)(η-1,5-cyclooctadiene)ruthenium(II), bis(methyl-3-oxopropanato)(η-1,5-cyclooctadiene)ruthenium(II), bis(ethyl-3-oxopropanato)(η-1,5-cyclooctadiene)ruthenium(II), bis(n-propyl-3-oxopropanato)(η-1,5-cyclooctadiene)ruthenium(II), bis(isopropyl-3-oxopropanato)(η-1,5-cyclooctadiene)ruthenium(II), bis(n-butyl-3-oxopropanato)(η-1,5-cyclooctadiene)ruthenium(II) and bis(t-butyl-3-oxopropanato)(η-1,5-cyclooctadiene)ruthenium(II).

Examples of compounds in which $R^1$ is a hydrocarbon group having 1 to 4 carbon atoms and $R^2$ is a halogenated alkoxy group having 1 to 4 carbon atoms include bis(trifluoromethyl-3-oxobutanato)(η-1,6-heptadiene)ruthenium(II), bis(pentafluoroethyl-3-oxobutanato)(η-1,6-heptadiene)ruthenium(II), bis(perfluoro-n-propyl-3-oxobutanato)(η-1,6-heptadiene)ruthenium(II), bis(perfluoroisopropyl-3-oxobutanato)(η-1,6-heptadiene)ruthenium(II), bis(perfluoro-n-butyl-3-oxobutanato)(η-1,6-heptadiene)ruthenium(II), bis(perfluoro-t-butyl-3-oxobutanato)(η-1,6-heptadiene) ruthenium(II), bis(trifluoromethyl-3-oxobutanato)(η-1,7-octadiene)ruthenium(II), bis(pentafluoroethyl-3-oxobutanato)(η-1,7-octadiene)ruthenium(II), bis(perfluoro-n-propyl-3-oxobutanato)(η-1,7-octadiene)ruthenium(II), bis(perfluoroisopropyl-3-oxobutanato)(η-1,7-octadiene) ruthenium(II), bis(perfluoro-n-butyl-3-oxobutanato)(η-1,7-octadiene)ruthenium(II), bis(perfluoro-t-butyl-3-oxobutanato)(η-1,7-octadiene)ruthenium(II), bis(trifluoromethyl-3-oxobutanato)(η-1,4-cyclohexadiene) ruthenium(II), bis(pentafluoroethyl-3-oxobutanato)(η-1,4-cyclohexadiene)ruthenium(II), bis(perfluoro-n-propyl-3-oxobutanato)(η-1,4-cyclohexadiene)ruthenium(II), bis(perfluoroisopropyl-3-oxobutanato)(η-1,4-cyclohexadiene) ruthenium(II), bis(perfluoro-n-butyl-3-oxobutanato)(η-1,4-cyclohexadiene)ruthenium(II), bis(perfluoro-t-butyl-3-oxobutanato)(η-1,4-cyclohexadiene)ruthenium(II), bis(trifluoromethyl-3-oxopropanato)(η-1,4-cyclohexadiene) ruthenium(II), bis(pentafluoroethyl-3-oxopropanato)(η-1,4-cyclohexadiene)ruthenium(II), bis(perfluoro-n-propyl-3-oxopropanato)(η-1,4-cyclohexadiene)ruthenium(II), bis(perfluoroisopropyl-3-oxopropanato)(η-1,4-cyclohexadiene)ruthenium(II), bis(perfluoro-n-butyl-3-oxopropanato)(η-1,4-cyclohexadiene)ruthenium(II), bis(perfluoro-t-butyl-3-oxopropanato)(η-1,4-cyclohexadiene) ruthenium(II), bis(trifluoromethyl-3-oxobutanato)(η-1,5-cyclooctadiene)ruthenium(II), bis(pentafluoroethyl-3-oxobutanato)(η-1,5-cyclooctadiene)ruthenium(II), bis(perfluoro-n-propyl-3-oxobutanato)(η-1,5-cyclooctadiene) ruthenium(II), bis(perfluoroisopropyl-3-oxobutanato)(η-1,5-cyclooctadiene)ruthenium(II), bis(perfluoro-n-butyl-3-oxobutanato)(η-1,5-cyclooctadiene)ruthenium(II), bis(perfluoro-t-butyl-3-oxobutanato)(η-1,5-cyclooctadiene) ruthenium(II), bis(trifluoromethyl-3-oxopropanato)(η-1,5-cyclooctadiene)ruthenium(II), bis(pentafluoroethyl-3-oxopropanato)(η-1,5-cyclooctadiene)ruthenium(II), bis(perfluoro-n-propyl-3-oxopropanato)(η-1,5-cyclooctadiene) ruthenium(II), bis(perfluoroisopropyl-3-oxopropanato)(η-1,5-cyclooctadiene)ruthenium(II), bis(perfluoro-n-butyl-3-oxopropanato)(η-1,5-cyclooctadiene)ruthenium(II) and bis(perfluoro-t-butyl-3-oxopropanato)(η-1,5-cyclooctadiene) ruthenium(II).

Examples of compounds in which $R^1$ is a halogenated hydrocarbon group having 1 to 4 carbon atoms and $R^2$ is a halogenated hydrocarbon group having 1 to 4 carbon atoms include bis(1,1,1,5,5,6,6,6-octafluoro-2,4-hexanedionato)(η-1,6-heptadiene)ruthenium(II), bis(1,1,1,5,5,6,6,6-octafluoro-2,4-hexanedionato)(η-1,7-octadiene)ruthenium(II), bis(1,1,1,5,5,5-hexafluoro-2,4-pentanedionato)(η-1,7-octadiene)ruthenium(II) and bis(1,1,1,2,2,6,6,7,7,7-decafluoro-3,5-pentanedionato)(η-1,7-octadiene)ruthenium(II).

Examples of compounds in which $R^1$ is a halogenated hydrocarbon group having 1 to 4 carbon atoms and $R^2$ is an alkoxy group having 1 to 4 carbon atoms include bis(methyl-3-oxo-4,4,4-trifluorobutanato)(η-1,6-heptadiene)ruthenium(II), bis(ethyl-3-oxo-4,4,4-trifluorobutanato)(η-1,6-heptadiene)ruthenium(II), bis(n-propyl-3-oxo-4,4,4-trifluorobutanato)(η-1,6-heptadiene)ruthenium(II), bis(isopropyl-3-oxo-4,4,4-trifluorobutanato)(η-1,6-heptadiene)ruthenium(II), bis(t-butyl-3-oxo-4,4,4-trifluorobutanato)(η-1,6-heptadiene)ruthenium(II), bis(methyl-3-oxo-4,4,5,5,5-pentafluoropentanato)(η-1,6-heptadiene)ruthenium(II), bis(ethyl-3-oxo-4,4,5,5,5-pentafluoropentanato)(η-1,6-heptadiene)ruthenium(II), bis(n-propyl-3-oxo-4,4,5,5,5-pentafluoropentanato)(η-1,6-heptadiene)ruthenium(II), bis(isopropyl-3-oxo-4,4,5,5,5-pentafluoropentanato)(η-1,6-heptadiene)ruthenium(II), bis(n-butyl-3-oxo-4,4,5,5,5-pentafluoropentanato)(η-1,6-heptadiene)ruthenium(II), bis(methyl-3-oxo-4,4,4-trifluorobutanato)(η-1,7-octadiene)ruthenium(II), bis(ethyl-3-oxo-4,4,4-trifluorobutanato)(η-1,7-octadiene)ruthenium(II), bis(n-propyl-3-oxo-4,4,4-trifluorobutanato)(η-1,7-octadiene)ruthenium(II), bis(isopropyl-3-oxo-4,4,4-trifluorobutanato)(η-1,7-octadiene)ruthenium(II), bis(t-butyl-3-oxo-4,4,4-trifluorobutanato)(η-1,7-octadiene)

ruthenium(II), bis(methyl-3-oxo-4,4,5,5,5-pentafluoropentanato)(η-1,7-octadiene)ruthenium(II), bis(ethyl-3-oxo-4,4,5,5,5-pentafluoropentanato)(η-1,7-octadiene)ruthenium(II), bis(n-propyl-3-oxo-4,4,5,5,5-pentafluoropentanato)(η-1,7-octadiene)ruthenium(II), bis(isopropyl-3-oxo-4,4,5,5,5-pentafluoropentanato)(η-1,7-octadiene)ruthenium(II), bis(n-butyl-3-oxo-4,4,5,5,5-pentafluoropentanato)(η-1,7-octadiene)ruthenium(II), bis(methyl-3-oxo-4,4,4-trifluorobutanato)(η-1,4-cyclohexadiene)ruthenium(II), bis(ethyl-3-oxo-4,4,4-trifluorobutanato)(η-1,4-cyclohexadiene)ruthenium(II), bis(n-propyl-3-oxo-4,4,4-trifluorobutanato)(η-1,4-cyclohexadiene)ruthenium(II), bis(isopropyl-3-oxo-4,4,4-trifluorobutanato)(η-1,4-cyclohexadiene)ruthenium(II), bis(t-butyl-3-oxo-4,4,4-trifluorobutanato)(η-1,4-cyclohexadiene)ruthenium(II), bis(methyl-3-oxo-4,4,5,5,5-pentafluoropentanato)(η-1,4-cyclohexadiene)ruthenium(II), bis(ethyl-3-oxo-4,4,5,5,5-pentafluoropentanato)(η-1,4-cyclohexadiene)ruthenium(II), bis(n-propyl-3-oxo-4,4,5,5,5-pentafluoropentanato)(η-1,4-cyclohexadiene)ruthenium(II), bis(isopropyl-3-oxo-4,4,5,5,5-pentafluoropentanato)(η-1,4-cyclohexadiene)ruthenium(II), bis(n-butyl-3-oxo-4,4,5,5,5-pentafluoropentanato)(η-1,4-cyclohexadiene)ruthenium(II), bis(methyl-3-oxo-4,4,4-trifluorobutanato)(η-1,5-cyclooctadiene)ruthenium(II), bis(ethyl-3-oxo-4,4,4-trifluorobutanato)(η-1,5-cyclooctadiene)ruthenium(II), bis(n-propyl-3-oxo-4,4,4-trifluorobutanato)(η-1,5-cyclooctadiene)ruthenium(II), bis(isopropyl-3-oxo-4,4,4-trifluorobutanato)(η-1,5-cyclooctadiene)ruthenium(II), bis(t-butyl-3-oxo-4,4,4-trifluorobutanato)(η-1,5-cyclooctadiene)ruthenium(II), bis(methyl-3-oxo-4,4,5,5,5-pentafluoropentanato)(η-1,5-cyclooctadiene)ruthenium(II), bis(ethyl-3-oxo-4,4,5,5,5-pentafluoropentanto)(η-1,5-cyclooctadiene)ruthenium(II), bis(n-propyl-3-oxo-4,4,5,5,5-pentafluoropentanato)(η-1,5-cyclooctadiene)ruthenium(II), bis(isopropyl-3-oxo-4,4,5,5,5-pentafluoropentanato)(η-1,5-cyclooctadiene)ruthenium(II) and bis(n-butyl-3-oxo-4,4,5,5,5-pentafluoropentanto)(η-1,5-cyclooctadiene)ruthenium(II).

Examples of compounds in which $R^1$ is a halogenated hydrocarbon group having 1 to 4 carbon atoms and $R^2$ is a halogenated alkoxy group having 1 to 4 carbon atoms include bis(trifluoromethyl-3-oxo-4,4,4-trifluorobutanato)(η-1,6-heptadiene)ruthenium(II), bis(pentafluoroethyl-3-oxo-4,4,4-trifluorobutanato)(η-1,6-heptadiene)ruthenium(II), bis(perfluoro-n-propyl-3-oxo-4,4,4-trifluorobutanato)(η-1,6-heptadiene)ruthenium(II), bis(perfluoroisopropyl-3-oxo-4,4,4-trifluorobutanato)(η-1,6-heptadiene)ruthenium(II), bis(perfluoro-t-butyl-3-oxo-4,4,4-trifluorobutanato)(η-1,6-heptadiene)ruthenium(II), bis(trifluoromethyl-3-oxo-4,4,5,5,5-pentafluoropentanato)(η-1,6-heptadiene)ruthenium(II), bis(pentafluoroethyl-3-oxo-4,4,5,5,5-pentafluoropentanato)(η-1,6-heptadiene)ruthenium(II), bis(perfluoro-n-propyl-3-oxo-4,4,5,5,5-pentafluoropentanato)(η-1,6-heptadiene)ruthenium(II), bis(perfluoroisopropyl-3-oxo-4,4,5,5,5-pentafluoropentanato)(η-1,6-heptadiene)ruthenium(II), bis(perfluoro-n-butyl-3-oxo-4,4,5,5,5-pentafluoropentanato)(η-1,6-heptadiene)ruthenium(II), bis(trifluoromethyl-3-oxo-4,4,4-trifluorobutanato)(η-1,7-octadiene)ruthenium(II), bis(pentafluoroethyl-3-oxo-4,4,4-trifluorobutanato)(η-1,7-octadiene)ruthenium(II), bis(perfluoro-n-propyl-3-oxo-4,4,4-trifluorobutanato)(η-1,7-octadiene)ruthenium(II), bis(perfluoroisopropyl-3-oxo-4,4,4-trifluorobutanato)(η-1,7-octadiene)ruthenium(II), bis(perfluoro-t-butyl-3-oxo-4,4,4-trifluorobutanato)(η-1,7-octadiene)ruthenium(II), bis(trifluoromethyl-3-oxo-4,4,5,5,5-pentafluoropentanato)(η-1,7-octadiene)ruthenium(II), bis(pentafluoroethyl-3-oxo-4,4,5,5,5-pentafluoropentanato)(η-1,7-octadiene)ruthenium(II), bis(perfluoro-n-propyl-3-oxo-4,4,5,5,5-pentafluoropentanato)(η-1,7-octadiene)ruthenium(II), bis(perfluoroisopropyl-3-oxo-4,4,5,5,5-pentafluoropentanato)(η-1,7-octadiene)ruthenium(II), bis(perfluoro-n-butyl-3-oxo-4,4,5,5,5-pentafluoropentanato)(η-1,7-octadiene)ruthenium(II), bis(trifluoromethyl-3-oxo-4,4,4-trifluorobutanato)(η-1,4-cyclohexadiene)ruthenium(II), bis(pentafluoroethyl-3-oxo-4,4,4-trifluorobutanato)(η-1,4-cyclohexadiene)ruthenium(II), bis(perfluoro-n-propyl-3-oxo-4,4,4-trifluorobutanato)(η-1,4-cyclohexadiene)ruthenium(II), bis(perfluoroisopropyl-3-oxo-4,4,4-trifluorobutanato)(η-1,4-cyclohexadiene)ruthenium(II), bis(perfluoro-t-butyl-3-oxo-4,4,4-trifluorobutanato)(η-1,4-cyclohexadiene)ruthenium(II), bis(trifluoromethyl-3-oxo-4,4,5,5,5-pentafluoropentanato)(η-1,4-cyclohexadiene)ruthenium(II), bis(pentafluoroethyl-3-oxo-4,4,5,5,5-pentafluoropentanato)(η-1,4-cyclohexadiene)ruthenium(II), bis(perfluoro-n-propyl-3-oxo-4,4,5,5,5-pentafluoropentanato)(η-1,4-cyclohexadiene)ruthenium(II), bis(perfluoroisopropyl-3-oxo-4,4,5,5,5-pentafluoropentanato)(η-1,4-cyclohexadiene)ruthenium(II), bis(perfluoro-n-butyl-3-oxo-4,4,5,5,5-pentafluoropentanato)(η-1,4-cyclohexadiene)ruthenium(II), bis(trifluoromethyl-3-oxo-4,4,4-trifluorobutanato)(η-1,5-cyclooctadiene)ruthenium(II), bis(pentafluoroethyl-3-oxo-4,4,4-trifluorobutanato)(η-1,5-cyclooctadiene)ruthenium(II), bis(perfluoro-n-propyl-3-oxo-4,4,4-trifluorobutanato)(η-1,5-cyclooctadiene)ruthenium(II), bis(perfluoroisopropyl-3-oxo-4,4,4-trifluorobutanato)(η-1,5-cyclooctadiene)ruthenium(II), bis(perfluoro-t-butyl-3-oxo-4,4,4-trifluorobutanato)(η-1,5-cyclooctadiene)ruthenium(II), bis(trifluoromethyl-3-oxo-4,4,5,5,5-pentafluoropentanato)(η-1,5-cyclooctadiene)ruthenium(II), bis(pentafluoroethyl-3-oxo-4,4,5,5,5-pentafluoropentanato)(η-1,5-cyclooctadiene)ruthenium(II), bis(perfluoro-n-propyl-3-oxo-4,4,5,5,5-pentafluoropentanato)(η-1,5-cyclooctadiene)ruthenium(II), bis(perfluoroispropyl-3-oxo-4,4,5,5,5-pentafluoropentanato)(η-1,5-cyclooctadiene)ruthenium(II) and bis(perfluoro-n-butyl-3-oxo-4,4,5,5,5-pentafluoropentanato)(η-1,5-cyclooctadiene)ruthenium(II).

These compounds may be used singly, or two or more may be mixed and used together, as the ruthenium film-forming material. The use of one compound alone as the ruthenium film-forming material is preferred.

Alternatively, the ruthenium film-forming material of the invention may be used after dissolution in a solvent. The solvent employed for this purpose is not subject to any particular limitation, so long as it is a solvent which dissolves the compound of formula (1). Such solvents are exemplified by hydrocarbon solvents, halogenated hydrocarbon solvents, ether solvents, alcohol solvents and ketone solvents.

Examples of hydrocarbon solvents include n-pentane, cyclopentane, n-hexane, cyclohexane, n-heptane, cycloheptane, n-octane, cyclooctane, decane, cyclodecane, hydrogenated dicyclopentadiene, benzene, toluene, xylene, durene, indene, tetrahydronaphthalene and decahydronaphthalene.

Examples of the halogenated hydrocarbon solvent include dimethyldichloride, chloroform, carbon tetrachloride, tetrachloroethane, chlorobenzene, dichlorobenzene, tetrachlorobenzene, bromobenzene and fluorobenzene.

Examples of ether solvents include diethyl ether, dipropyl ether, dibutyl ether, ethylene glycol dimethyl ether, ethylene glycol diethyl ether, ethylene glycol methyl ethyl ether, diethylene glycol dimethyl ether, diethylene glycol diethyl ether, diethylene glycol methyl ethyl ether, tetrahydrofuran, tetrahydropyran, bis(2-methoxyethyl) ether, p-dioxane, butyl glycidyl ether, anisole, 2-methylanisole, 3-methylanisole, 4-methylanisole, phenetole, 2-methylphenetole, 3-methylphenetole, 4-methylphenetole, veratrole, 2-ethoxyanisole and 1,4-dimethoxybenzene.

Examples of alcohol solvents include methanol, ethanol, n-propanol, i-propanol, allyl alcohol, n-butanol, i-butanol, t-butanol, n-heptanol, octanol, diethylene glycol, 1,2-butanediol, 1,3-butanediol, propylene glycol, cyclopentanol, cyclohexanol, phenol and 3-chloro-1-propanol.

Examples of ester solvents include ethyl acetate, methyl acetate, vinyl acetate, methyl methacrylate, ethyl chloroacetate, ethyl acetoacetate, methyl chlorocarbonate and ethyl chlorocarbonate.

Examples of ketone solvents include acetone, methyl ethyl ketone, acetylacetone, diethyl ketone, methyl hexyl ketone and cyclohexanone.

These solvents may be used singly or as mixtures of two or more thereof.

Among these solvents, from the standpoint of solubility and the stability of the resulting solution of the composition, the use of a hydrocarbon solvent, an ether solvent, an ester solvent, a ketone solvent or a mixed solvent from a combination of these solvents is preferred. Examples of the hydrocarbon solvents preferred for use include cyclohexane, n-heptane, cycloheptane, n-octane, benzene, toluene and xylene. In the case of ether solvents, the use of diethyl ether, dipropyl ether, dibutyl ether, ethylene glycol diethyl ether, ethylene glycol methyl ethyl ether, tetrahydrofuran, tetrahydropyran, anisole, 2-methylanisole, 3-methylanisole, 4-methylanisole, phenetole, veratrole, 2-ethoxyanisole or 1,4-dimethoxybenzene is preferred. In the case of ester solvents, the use of ethyl acetate is preferred. In the case of ketone solvents, the use of acetone, methyl ethyl ketone or acetylacetone is preferred.

When the ruthenium film-forming material of the invention is dissolved in a solvent and used, the ratio of the combined weight of the ingredients, exclusive of the solvent, in the total weight of the composition (referred to below as the "solids concentration"), is preferably from 0.1 to 70 wt %, and more preferably from 20 to 50 wt %.

Aside from the compound of formula (1), the ruthenium film-forming material of the invention may include also other ruthenium compounds. Examples of such other ruthenium compounds include ruthenium dodecacarbonyl, (2,3-dimethyl-1,3-butandiene)tricarbonyl ruthenium, (1,3-butadiene) tricarbonyl ruthenium, (1,3-cyclohexadiene)tricarbonyl ruthenium, (1,4-cyclohexadiene)tricarbonyl ruthenium and (1,5-cyclooctadiene)tricarbonyl ruthenium.

The ratio of the weight of the compound of formula (1) in the combined weight of all the ingredients exclusive of the solvent in the ruthenium film-forming material of the invention is preferably 30 to 100 wt %, more preferably 50 to 100 wt %, even more preferably 70 to 100 wt %, still more preferably 80 to 100 wt %, and most preferably 90 to 100 wt %.

The ruthenium film-forming method of the invention is a method which uses the ruthenium film-forming material described above.

Aside from employing the above ruthenium film-forming material, the ruthenium film-forming method of the invention may make use of a method that is already known to the art. For example, the method of the invention may be carried out as follows.

One example of the ruthenium film-forming method of the invention includes the steps of: (1) vaporizing the ruthenium film-forming material of the invention under reduced pressure and applied heat, and supplying the vaporized material (i.e. mist) onto a base (e.g., a substrate), and then (2) heating and thereby thermally decomposing the ruthenium film-forming material which has been supplied onto the base so as to form a ruthenium film on the base. Even should decomposition of the ruthenium film-forming material of the invention occur in above-described Step (1), this will not diminish the effects of the invention.

Suitable materials such as glass, silicon semiconductor, quartz, metal, metal oxides and synthetic resin may be used here as the base material, although a material capable of withstanding the temperature of the ruthenium compound thermal decomposition in above-described Step (2) is preferred.

Specifically, the base is composed of a metal film (e.g., tantalum (Ta), titanium (Ti), zirconium (Zr), hafnium (Hf), platinum (Pt), iridium (Ir), copper (Cu), gold (Au), aluminum (Al)), a metal nitride film (e.g., TaN, TiN, ZrN, AlN), or a dielectric film.

Examples of dielectric films include thermal oxide films, plasma-enhanced TEOS films (PETEOS films), high-density plasma-enhanced TEOS films (HDP films), silicon oxide films obtained by thermal chemical vapor deposition (thermal CVD), boron phosphate silicate glass films (BPSG films), dielectric films made of fluorosilicate glass (FSG), and dielectric films having low dielectric constant (i.e. low-k).

The thermal oxide films are formed by exposing silicon which has been brought to a high temperature to an oxidizing atmosphere, and chemically reacting the silicon with oxygen, or silicon with water.

The PETEOS films are formed by chemical vapor deposition using tetraethyl orthosilicate (TEOS) as the precursor and utilizing a plasma as the reaction-promoting conditions.

The HDP films are formed by chemical vapor deposition using tetraethyl orthosilicate (TEOS) as the precursor and utilizing a high-density plasma as the reaction-promoting conditions.

The silicon oxide films obtained by thermal CVD are formed by ordinary pressure CVD (AP-CVD) or low-pressure CVD (LP-CVD).

The boron phosphate silicate glass films (BPSG films) can be obtained by atmospheric-pressure CVD (AP-CVD) or low-pressure CVD (LP-CVD).

The dielectric films, which are named FSG, can be formed by chemical vapor deposition using a high-density plasma as the reaction-promoting conditions.

Examples of materials which form the above-described low-k dielectric films include organic SOG, hydrogen-containing SOG, low-k materials composed of organic polymers, SiOF-based low-k materials and SiOC-based low-k materials. Here, "SOG" is an abbreviation for "spin-on-glass," and refers to a dielectric film material obtained by coating a precursor onto a base, followed by film formation via heat treatment and the like.

The organic SOG is composed of, for example, a silicon oxide containing organic groups such as methyl groups. Here, the dielectric film may be obtained by coating a precursor which includes, for example, a mixture of tetraethoxysilane and methyltrimethoxysilane onto a base, followed by heat treatment and the like.

The hydrogen-containing SOG is composed of silicon oxide containing silicon-hydrogen bonds. Here, the dielectric film may be obtained by coating a precursor which includes, for example, triethoxysilane and the like onto a base, followed by heat treatment and the like.

Illustrative examples of low-k materials made of organic polymers include low-k materials composed primarily of polyarylene, polyimide, polybenzocyclobutene or polyfluorinated ethylene.

The SiOF-based low-k material is composed of a silicon oxide which contains fluorine atoms, and may be obtained by doping the silicon oxide obtained by chemical vapor deposition with fluorine.

The SiOC-based low-k material is composed of a silicon oxide which contains carbon atoms, and may be obtained by chemical vapor deposition using, for example, a mixture of silicon tetrachloride and carbon monoxide as the precursor.

Among the above dielectric films, those dielectric films formed using organic SOG, hydrogen-containing SOG or a low-k material composed of an organic polymer may have small pores in the film.

The base on which a ruthenium film is formed may have trenches. The trenches are formed by a known method, such as photolithography, on the base, which is composed of a material such as those mentioned above.

The trenches may be of any shape and size, although the advantageous effects of the invention are maximally exhibited in cases where the width of the trench openings (i.e. the smallest distance across the trench surface openings) is 300 nm or less and the trench aspect ratio, defined as the trench depth divided by the smallest distance across the trench surface openings, is 3 or more. The width of the trench openings is preferably from 10 to 250 nm, and more preferably from 30 to 200 nm. The trench aspect ratio is preferably from 3 to 40, and more preferably from 5 to 25.

In Step (1) above, the ruthenium compound is vaporized at a temperature of preferably from 30 to 350° C., and more preferably from 50 to 300° C.

In Step (2), the ruthenium film-forming material is thermally decomposed at a temperature of preferably from 100 to 800° C., more preferably from 100 to 600° C., even more preferably from 180 to 450° C., still more preferably from 200 to 420° C., and most preferably from 250 to 410° C.

The ruthenium film-forming method of the invention may be carried out under any of the following conditions: in the presence or absence of an inert gas, or in the presence or absence of a reducing gas. Alternatively, it may be carried out in the presence of both an inert gas and a reducing gas. Here, examples of the inert gas include nitrogen, argon and helium. Examples of the reducing gas include hydrogen gas and ammonia gas. Moreover, the ruthenium film-forming method of the invention may be carried out with an oxidizing gas also present. Examples of the oxidizing gas include oxygen, carbon monoxide and nitrous oxide.

In order to reduce the amount of impurities in the ruthenium film that has formed, it is especially preferable to have these reducing gases also present in the atmosphere during film formation. In cases where a reducing gas is made present during film formation, the proportion of reducing gas in the atmosphere is preferably from 1 to 100 mol %, and more preferably from 3 to 100 mol %.

The proportion of oxidizing gas in the atmosphere is preferably 10 mol % or less, more preferably 1 mol % or less, and even more preferably 0.1 mol % or less.

The chemical vapor deposition process of the invention may be carried out under applied pressure, atmospheric pressure or reduced pressure. Among these conditions, the process is preferably carried out under atmospheric pressure or reduced pressure, and is more preferably carried out under a pressure of 15,000 Pa or less.

Another example of the ruthenium film-forming method of the invention is a process in which the above-described ruthenium film-forming material is coated onto a base, and then the applied material is subjected to heat treatment and/or light treatment, thereby converting the compound of general formula (1) on the base into a ruthenium film.

When the above-described ruthenium film-forming material is coated onto a base of the type mentioned above, a suitable method such as spincoating, roll coating, curtain coating, dip coating, spraying or a droplet jetting process may be used. In these coating operations, depending on the size and shape on the base, coating conditions are employed such that the ruthenium film-forming material extends to all corners of the base. For example, in cases where spin coating is employed as the coating method, the rotational speed of the spinner may be set to 300 to 2,500 rpm, and preferably 500 to 2,000 rpm.

After the above coating operation, heat treatment may be carried out in order to remove low-boiling ingredients such as solvents which are included in the ruthenium film-forming material that has been applied. The heating temperature and time will vary depending on the type and boiling point (vapor pressure) of the solvent used, but may be set to, for example, 100 to 350° C. for 5 to 90 minutes. Here, solvent removal may be carried out at a lower temperature by reducing the pressure of the overall system. The heating temperature and time are preferably 100 to 250° C. for 10 to 60 minutes.

Next, a ruthenium film is formed on the base by heat-treating and/or light-treating the coating film that has been formed as described above.

The temperature of the heat treatment is preferably from 100 to 800° C., more preferably from 150 to 600° C., and even more preferably from 300 to 500° C. The heat treatment time is preferably from 30 seconds to 120 minutes, more preferably from 1 to 90 minutes, and even more preferably from 10 to 60 minutes.

Exemplary light sources which may used in the above light treatment (e.g., light irradiation) include mercury vapor lamps, deuterium lamps, rare-gas discharge lamps, YAG lasers, argon lasers, carbon dioxide lasers and rare gas-halogen excimer lasers. Examples of mercury vapor lamps include low-pressure mercury vapor lamps and high-pressure mercury vapor lamps. Examples of the rare gas used in the rare gas discharge lamps include argon, krypton and xenon. Examples of the rare gas-halogen used in the rare gas-halogen excimer lasers include XeF, XeCl, XeBr, KrF, KrCl, ArF and ArCl.

These light sources have an output of preferably 10 to 5,000 W, and more preferably 100 to 1,000 W. The wavelength of these light sources, although not subject to any particular limitation, is preferably from 170 to 600 nm. From the standpoint of the quality of the ruthenium film to be formed, the use of laser light is especially preferred. To form an even better ruthenium film, plasma oxidation may be carried out in an oxidizing gas atmosphere. Examples of the plasma oxidizing conditions in such a case are as follows: an RF power of 20 to 100 W; an inlet gas which includes 90 to 100% of oxygen, with the balance being argon; an inlet pressure of 0.05 to 0.2 Pa for the inlet gas, and a plasma oxidation time of 10 to 240 seconds.

The atmosphere in the coating operation and during heat treatment and/or light treatment is preferably composed of inert gases such as nitrogen, helium and argon. In addition, a reducing gas such as hydrogen or ammonia may be admixed where necessary.

One or the other of the above heat treatment and light treatment may be carried out, or both heat treatment and light treatment may be carried out. When both heat treatment and light treatment are carried out, the order in which they are carried out is not important (i.e. any one of them can be carried out first); heat treatment and light treatment may even be carried out at the same time. Of these possibilities, it is preferable either to carry out only heat treatment or to carry out both heat treatment and light treatment. To form an even better ruthenium film, plasma oxidation may be carried out separately from the above heat treatment and/or light treatment step.

The ruthenium film-forming material of the invention has an excellent long-term storage stability and heat stability. Even when this material is enclosed within an inert gas atmosphere in the precursor ampoule of a chemical vapor deposition system and held in a heated state at 100 to 150° C., deterioration of the material does not arise for about 15 days. This is highly advantageous for stabilizing the long-term continuous operation of a chemical vapor deposition system.

The ruthenium film obtained as described above has a high purity and electrical conductivity, enabling it to be advantageously used as, for example, a barrier film for wiring electrodes, a plating growth film or a capacitor electrode.

EXAMPLES

The invention is illustrated more fully by way of the following examples, although these examples do not in any way limit the invention.

Synthesis Example 1

Synthesis of Bis(Methyl-3-Oxo-4,4,4-Trifluorobutanato)(η-1,5-Cyclooctadiene)Ruthenium(II)

A nitrogen-flushed three-neck flask was charged with 65.36 g of ruthenium trichloride trihydrate, 500 mL of ethanol and 250 mL of 1,5-cyclooctadiene, and the flask contents were refluxed under heating at 85° C. for 5 hours. Following the completion of refluxing, the solution was cooled to room temperature, after which filtration was carried out. The resulting solid was washed with 500 mL of diethyl ether and dried in vacuo, yielding 70.02 g of (η-1,5-cyclooctadiene)ruthenium(II) dichloride as a brown solid. Next, 2.81 g of this (η-1,5-cyclooctadiene)ruthenium(II) dichloride, 6.38 g of sodium carbonate, 2.9 mL of methyl 3-oxo-4,4,4-trifluorobutanoate and 10 mL of ethanol were placed in a nitrogen-flushed three-neck flask and refluxed under heating at 85° C. for 2 hours. Following the completion of refluxing, the solution was cooled to room temperature, then alumina column chromatography (developing solvent: acetone) was carried out. The resulting solution was concentrated and dried under reduced pressure, and 3.61 g of bis(methyl-3-oxo-4,4,4-trifluorobutanato)(η-1,5-cyclooctadiene)ruthenium(II) was obtained as a black reddish-brown liquid. The yield was 66 wt %.

Synthesis Example 2

Synthesis of Bis(Ethyl-3-Fluoro-3-Oxopropionato)(η-1,5-Cyclooctadiene)Ruthenium(II)

Aside from using 2.8 mL of ethyl 3-fluoro-3-oxoproprionate instead of 2.9 mL of methyl 3-oxo-4,4,4-trifluorobutanoate, the same procedure as that in Synthesis Example 1 was followed, and 3.42 g of bis(ethyl-3-fluoro-3-oxopropionato)(η-1,5-cyclooctadiene)ruthenium(II) was obtained as a black yellowish-brown liquid. The yield was 72 wt %.

Synthesis Example 3

Synthesis of Bis(1,1,1-Trifluoro-2,4-Pentanedionato)(η-1,5-Cyclooctadiene)Ruthenium(II)

Aside from using 2.8 mL of 1,1,1-trifluoro-2,4-pentanedione instead of 2.9 mL of methyl 3-oxo-4,4,4-trifluorobutanoate, the same procedure as that in Synthesis Example 1 was followed, and 3.30 g of bis(1,1,1-trifluoro-2,4-pentanedionato)(η-1,5-cyclooctadiene)ruthenium(II) was obtained as a highly viscous blackish-brown liquid. The yield was 64 wt %.

Synthesis Example 4

Synthesis of Bis(Ethyl-3-Oxobutanato)(η-1,5-Cyclooctadiene)Ruthenium(II)

Aside from using 2.8 mL of ethyl 3-oxobutanoate instead of 2.9 mL of methyl 3-oxo-4,4,4-trifluorobutanoate, the same procedure as that in Synthesis Example 1 was followed, and 3.87 g of bis(ethyl-3-oxobutanato)(η-1,5-cyclooctadiene)ruthenium(II) was obtained as a blackish-brown liquid. The yield was 83 wt %.

Synthesis Example 5

Synthesis of Bis(Ethyl-3-Oxobutanato)(η-1,6-Heptadiene)Ruthenium(II)

A nitrogen-flushed three-neck flask was charged with 65.36 g of ruthenium trichloride trihydrate, 500 mL of ethanol and 270 mL of 1,6-heptadiene, and the flask contents were refluxed under heating at 85° C. for 5 hours. Following the completion of refluxing, the solution was cooled to room temperature, after which filtration was carried out. The resulting solid was washed with 500 mL of diethyl ether and dried in vacuo, yielding 63.04 g of (η-1,6-heptadiene)ruthenium(II) dichloride as a brown solid. Next, 2.52 g of this (η-1,6-heptadiene)ruthenium(II) dichloride, 6.38 g of sodium carbonate, 2.8 mL of ethyl 3-oxobutanoate and 10 mL of ethanol were placed in a nitrogen-flushed three-neck flask and refluxed under heating at 85° C. for 2 hours. Following the completion of refluxing, the solution was cooled to room temperature, then alumina column chromatography (developing solvent: acetone) was carried out. The resulting solution was concentrated and dried under reduced pressure, and 2.42 g of bis(ethyl-3-oxobutanato)(η-1,6-heptadiene)ruthenium(II) was obtained as a black reddish-brown liquid. The yield was 55 wt %.

Synthesis Example 6

Synthesis of Bis(2,4-Pentanedionato)(η-1,5-Cyclooctadiene)Ruthenium(II)

A nitrogen-flushed three-neck flask was charged with 65.36 g of ruthenium trichloride trihydrate, 500 mL of ethanol and 250 mL of 1,5-cyclooctadiene, and the flask contents were refluxed under heating at 85° C. for 5 hours. Following the completion of refluxing, the solution was cooled to room temperature, after which filtration was carried out. The resulting solid was washed with 500 mL of diethyl ether and dried in vacuo, yielding 70.02 g of (η-1,5-cyclooctadiene)ruthenium(II) dichloride as a brown solid. Next, 31.56 g of this (η-1,5-cyclooctadiene)ruthenium(II) dichloride, 34.97 g of sodium carbonate, 28 mL of 2,4-pentanedione and 100 mL of N,N-dimethylformamide were placed in a nitrogen-flushed three-neck flask and stirred at 140° C. for 1 hour. Following reaction completion, the solution was cooled to room temperature, then alumina column chromatography (developing solvent: diethyl ether) was carried out. The resulting solution was concentrated, after which 120 mL of water was added and the solution was left at rest for 3 hours. The crystals that precipitated out were collected by filtration, and after being washed with water, were dried in vacuo. 46.53 g of bis(2,4-pentanedionato)(η-1,5-cyclooctadiene)ruthenium(II) was obtained as an orangey-yellow solid. The yield was 94 wt %.

In the following examples, the resistivity was measured with a probe-type resistivity measuring instrument manufactured by Napson Corporation (model: RT-80/RG-80). The film thickness and film density were measured with a grazing incidence x-ray diffractometer manufactured by Philips (model: X'Pert MRD). The electron spectroscopy chemical analysis (ESCA) spectrum was measured with an instrument manufactured by JEOL Ltd. (model: JPS80). Adhesion was evaluated by the crosscut tape test in general accordance with JIS K-5400. A rating of "○" was assigned when no delamination whatsoever was observed between the substrate and the ruthenium film, and a rating of "x" was assigned when delamination was observed between the substrate and the ruthenium.

Example 1

(1-1) Formation of Ruthenium Film

The bis(methyl-3-oxo-4,4,4-trifluorobutanato)(η-1,5-cyclooctadiene)ruthenium(II) obtained in Synthesis Example 1 was measured out in an amount of 0.05 g into a quartz boat-type vessel within a nitrogen atmosphere, and set in a quartz reactor. A silicon wafer with a thermal oxide film was placed near the downstream side of the gas stream within the reactor and, at room temperature, nitrogen gas (hydrogen gas content: 3 vol %) was passed through the reactor at a flow rate of 300 mL/min for 20 minutes. The nitrogen gas within the reactor (hydrogen gas content: 3 vol %) was then passed through the reactor at a flow rate of 100 mL/min and the interior of the system was depressurized to 13 Pa, following which the reactor was heated at 80° C. for 5 minutes. A mist was generated from the boat-type vessel, and deposits on the quartz substrate that had been placed nearby were observed. After mist formation had ended, depressurization was stopped and nitrogen gas was introduced into the system to restore the pressure. Next, at a pressure of 101.3 kPa, nitrogen gas (hydrogen gas content: 3 vol %) was passed through at a flow rate of 200 mL/min, the reactor temperature was raised to 400° C., and the system was held in this state for one hour, whereupon a film having a metallic luster was obtained on the substrate. This film had a thickness of 0.05 μm.

The ESCA spectrum of this film was measured, whereupon peaks attributable to the $Ru_{3d}$ orbital were observed at 280 eV and 284 eV. No peaks from other elements were observed whatsoever, indicating that the film was metallic ruthenium. The resistivity of the ruthenium film was measured by the four-point probe method and found to be 48 μΩcm. The film had a film density of 11.7 g/cm³. The adhesion of the ruthenium film that has been formed here with the substrate was evaluated by the crosscut tape method, from which no delamination between the substrate and the ruthenium film was observed whatsoever. The results are shown in Table 1.

(1-2) Formation of Ruthenium Film

Aside from using hydrogen gas (100 vol %) instead of nitrogen gas (hydrogen gas content: 3 vol %), a film was formed in the same way as that in (1-1) above. As a result, a film having a metallic luster was obtained on the substrate. Upon measuring the ESCA spectrum of this film, peaks attributable to the $Ru_{3d}$ orbital were observed at 280 eV and 284 eV. No peaks from other elements were observed whatsoever, indicating that the film was metallic ruthenium. The various physical properties of the metallic ruthenium film thus obtained were evaluated in the same way as those in (1-1) above. The results are shown in Table 1.

(2) Storage Stability Test

To ascertain the storage stability, deterioration upon exposure to heat was investigated by carrying out accelerated testing under applied heat. One gram of bis(methyl-3-oxo-4,4,4-trifluorobutanato)(η-1,5-cyclooctadiene)ruthenium(II) was placed in a closed pressure vessel made of stainless steel and having a 50 mL capacity, the vessel was sealed under a nitrogen atmosphere and the interior of the system was depressurized to 13 Pa, following which the overall vessel was stored under heating at 110° C.

After holding the vessel for two weeks under 110° C. heating, no change was observed in the appearance of the bis(methyl-3-oxo-4,4,4-trifluorobutanato)(η-1,5-cyclooctadiene)ruthenium(II).

The vessel was then returned to room temperature and the vessel interior was flushed with dry nitrogen, following which film formation was carried out by the same procedure as that in (1-1) described above. As a result, a film having a metallic luster was obtained on the substrate. This film had a thickness of 0.05 μm.

Upon measuring the ESCA spectrum of the film, peaks attributable to the $Ru_{3d}$ orbital were observed at 280 eV and 284 eV. No peaks from other elements were observed whatsoever, indicating that the film was metallic ruthenium. The resistivity of the ruthenium film was measured by the four-point probe method and found to be 48 μΩcm. The film had a film density of 11.7 g/cm³. The adhesion of the ruthenium film that has been formed here with the substrate was evaluated by the crosscut tape method, from which no delamination between the substrate and the ruthenium film was observed whatsoever. Deterioration of the ruthenium metal film quality in the heating test was not observed. The results are shown in Table 1.

In addition, after holding the vessel for one month under heating at 110° C., no change was observed in the appearance of the bis(methyl-3-oxo-4,4,4-trifluorobutanato)(η-1,5-cyclooctadiene)ruthenium(II).

The vessel was then returned to room temperature and the vessel interior was flushed with dry nitrogen, following which film formation was carried out by the same procedure as that in (1-1) described above. As a result, a film having a metallic luster was obtained on the substrate. This film had a thickness of 0.04 μm. Upon measuring the ESCA spectrum of this film, peaks attributable to the $Ru_{3d}$ orbital were observed at 280 eV and 284 eV. No peaks from other elements were observed whatsoever, indicating that the film was metallic ruthenium. The resistivity of the ruthenium film was measured by the four-point probe method and found to be 75 μΩcm. The film had a film density of 10.8 g/cm³. The adhesion of the ruthenium film that has been formed here with the substrate was evaluated by the crosscut tape method, from which no delamination between the substrate and the ruthenium film was observed whatsoever. The results are shown in Table 1.

(3) Test of Vaporization Characteristics

To check the vaporization characteristics, the amount of vaporization was measured by the following test method. Within a glovebox having a dry nitrogen atmosphere and under room temperature, 1 g of bis(methyl-3-oxo-4,4,4-trifluorobutanato)(η-1,5-cyclooctadiene)ruthenium(II) was placed in a 100 mL stainless steel pressure vessel equipped with a valve, and the vessel was closed with an airtight stopper. Next, the vessel was placed on a hot plate, the valve was opened, and the vessel interior was depressurized at 13 Pa for 5 minutes while heating at 80° C. The valve was then closed, subsequent to which the vessel was allowed to cool for 3 hours, returning the vessel to room temperature. Next, within the glovebox, the valve was gradually opened and the pressure within the vessel was returned to atmospheric pressure. The vessel was then opened and the amount of vaporization during depressurizing treatment was calculated by measuring the amount of remaining material. The amount of vaporization was found to be 0.85 g. The results are shown in Table 1.

Example 2

(1) Formation of Ruthenium Film

Aside from using 0.05 g of the bis(ethyl-3-fluoro-3-oxopropionato)(η-1,5-cyclooctadiene)ruthenium(II) obtained in Synthesis Example 2 instead of 0.05 g of bis(methyl-3-oxo-4,4,4-trifluorobutanato)(η-1,5-cyclooctadiene)ruthenium (II), a film having metallic luster was obtained on the substrate in the same way as that in (1-1) and (1-2) of Example 1. The various properties of the resulting metallic ruthenium film were evaluated in the same way as those in Example 1. The results are shown in Table 1.

(2) Storage Stability Test

To ascertain the storage stability, aside from using 1 g of the bis(ethyl-3-fluoro-3-oxopropionato)(η-1,5-cyclooctadiene) ruthenium(II) obtained in Synthesis Example 2 instead of 1 g of bis(methyl-3-oxo-4,4,4-trifluorobutanato)(η-1,5-cyclooctadiene)ruthenium(II), deterioration upon exposure to heat was investigated by carrying out accelerated testing under applied heat in the same way as that in Example 1. The storage stability and the various properties of the metallic ruthenium film obtained were evaluated in the same way as those in Example 1. The results are shown in Table 1.

(3) Test of Vaporization Characteristics

To check the vaporization characteristics, aside from using 1 g of the bis(ethyl-3-fluoro-3-oxopropionato)(η-1,5-cyclooctadiene)ruthenium(II) obtained in Synthesis Example 2 instead of 1 g of bis(methyl-3-oxo-4,4,4-trifluorobutanato) (η-1,5-cyclooctadiene)ruthenium(II), the amount of vaporization was measured in the same way as that in Example 1. The results are shown in Table 1.

Example 3

(1) Formation of Ruthenium Film

Aside from using 0.05 g of the bis(1,1,1-trifluoro-2,4-pentanedionato)(η-1,5-cyclooctadiene)ruthenium(II) obtained in Synthesis Example 3 instead of 0.05 g of bis(methyl-3-oxo-4,4,4-trifluorobutanato)(η-1,5-cyclooctadiene)ruthenium(II), a film having metallic luster was obtained on the substrate in the same way as that in (1-1) and (1-2) of Example 1. The various properties of the resulting metallic ruthenium film were evaluated in the same way as those in Example 1. The results are shown in Table 1.

(2) Storage Stability Test

To ascertain the storage stability, aside from using 1 g of the bis(1,1,1-trifluoro-2,4-pentanedionato)(η-1,5-cyclooctadiene)ruthenium(II) obtained in Synthesis Example 3 instead of 1 g of bis(methyl-3-oxo-4,4,4-trifluorobutanato)(η-1,5-cyclooctadiene)ruthenium(II), deterioration upon exposure to heat was investigated by carrying out accelerated testing under applied heat in the same way as that in Example 1. The storage stability and the various properties of the metallic ruthenium film obtained were evaluated in the same way as those in Example 1. The results are shown in Table 1.

(3) Test of Vaporization Characteristics

To check the vaporization characteristics, aside from using 1 g of the bis(1,1,1-trifluoro-2,4-pentanedionato)(η-1,5-cyclooctadiene)ruthenium(II) obtained in Synthesis Example 3 instead of 1 g of bis(methyl-3-oxo-4,4,4-trifluorobutanato) (η-1,5-cyclooctadiene)ruthenium(II), the amount of vaporization was measured in the same way as that in Example 1. The results are shown in Table 1.

Example 4

(1) Formation of Ruthenium Film

Aside from using 0.05 g of the bis(ethyl-3-oxobutanato) (η-1,5-cyclooctadiene)ruthenium(II) obtained in Synthesis Example 4 instead of 0.05 g of bis(methyl-3-oxo-4,4,4-trifluorobutanato)(η-1,5-cyclooctadiene)ruthenium(II), a film having metallic luster was obtained on the substrate in the same way as that in (1-1) and (1-2) of Example 1. The various properties of the resulting metallic ruthenium film were evaluated in the same way as those in Example 1. The results are shown in Table 1.

(2) Storage Stability Test

To ascertain the storage stability, deterioration upon exposure to heat was investigated by carrying out accelerated testing under applied heat. One gram of bis(ethyl-3-oxobutanato)(η-1,5-cyclooctadiene)ruthenium(II) was placed in a closed pressure vessel made of stainless steel and having a 50 mL capacity, the vessel was sealed under a nitrogen atmosphere and the interior of the system was depressurized to 13 Pa, following which the overall vessel was stored under heating at 110° C. Even after one month, no change was observed in the appearance of the bis(ethyl-3-oxobutanato)(η-1,5-cyclooctadiene)ruthenium(II).

The vessel was then returned to room temperature and the vessel interior was flushed with dry nitrogen, following which film formation was carried out by the same procedure as that in (1-1) of Example 1, whereupon a film having a metallic luster was obtained on the substrate. The various properties of the resulting metallic ruthenium film were evaluated in the same way as those in Example 1. The results are shown in Table 1.

(3) Test of Vaporization Characteristics

To check the vaporization characteristics, aside from using 1 g of the bis(ethyl-3-oxobutanato)(η-1,5-cyclooctadiene)ruthenium(II) obtained in Synthesis Example 4 instead of 1 g of bis(methyl-3-oxo-4,4,4-trifluorobutanato)(η-1,5-cyclooctadiene)ruthenium(II), the amount of vaporization was measured in the same way as that in Example 1. The results are shown in Table 1.

Example 5

(1) Formation of Ruthenium Film

Aside from using 0.05 g of the bis(ethyl-3-oxobitanato)(η-1,6-heptadiene)ruthenium(II) obtained in Synthesis Example 5 instead of 0.05 g of bis(methyl-3-oxo-4,4,4-trifluorobutanatо)(η-1,5-cyclooctadiene)ruthenium(II), a film having metallic luster was obtained on the substrate in the same way as that in (1-1) and (1-2) of Example 1. The various properties of the resulting metallic ruthenium film were evaluated in the same way as those in Example 1. The results are shown in Table 1.

(2) Storage Stability Test

To ascertain the storage stability, deterioration upon exposure to heat was investigated by carrying out accelerated testing under applied heat. One gram of bis(ethyl-3-oxobutanato)(η-1,6-heptadiene)ruthenium(II) was placed in a closed pressure vessel made of stainless steel and having a 50 mL capacity, the vessel was sealed under a nitrogen atmosphere and the interior of the system was depressurized to 13 Pa, following which the overall vessel was stored under heating at 110° C. Even after one month, no change was observed in the appearance of the bis(ethyl-3-oxobutanato)(η-1,6-heptadiene)ruthenium(II).

The vessel was then returned to room temperature and the vessel interior was flushed with dry nitrogen, following which film formation was carried out by the same procedure as that in (1-1) of Example 1, whereupon a film having a metallic luster was obtained on the substrate. The various properties of the resulting metallic ruthenium film were evaluated in the same way as those in Example 1. The results are shown in Table 1.

(3) Test of Vaporization Characteristics

To check the vaporization characteristics, aside from using 1 g of the bis(ethyl-3-oxobutanato)(η-1,6-heptadiene)ruthenium(II) obtained in Synthesis Example 5 instead of 1 g of bis(methyl-3-oxo-4,4,4-trifluorobutanato)(η-1,5-cyclooctadiene)ruthenium(II), the amount of vaporization was measured in the same way as that in Example 1. The results are shown in Table 1.

Example 6

The following experiment was carried out inside a glovebox having a dry nitrogen atmosphere. A silicon substrate was mounted on a spin coater, and after carrying out the dropwise addition of 2 mL of the bis(ethyl-3-oxobutanato)(η-1,5-cyclooctadiene)ruthenium(II) obtained in Synthesis Example 4, was spun at a rotational speed of 500 rpm for 10 seconds. The substrate was then heated for 10 minutes on a 150° C. hot plate. This was followed by 30 minutes of heating at 350° C., whereupon the surface of the substrate became covered with a film having a metallic luster. The film had a thickness of 0.042 μm.

Upon measuring the ESCA spectrum of this film, peaks attributable to the $Ru_{3d}$ orbital were observed at 280 eV and 284 eV. No peaks from other elements were observed whatsoever, indicating that the film was metallic ruthenium. The resistivity of the ruthenium film was measured by the four-point probe method and found to be 121 μΩm. The film had a film density of 9.4 g/cm³. The adhesion to the substrate of the ruthenium film that has been formed here was evaluated by the crosscut tape method, from which no delamination between the substrate and the ruthenium film was observed whatsoever. The results are shown in Table 1.

Example 7

A ruthenium film-forming material containing 33 wt % of bis(ethyl-3-oxobutanato)(η-1,5-cyclooctadiene)ruthenium (II) was prepared by adding dried toluene to 1.00 g of the bis(ethyl-3-oxobutanato)(η-1,5-cyclooctadiene)ruthenium (II) obtained in Synthesis Example 4 so as to bring the total amount to 3.00 g.

Aside from using the ruthenium film-forming material containing 33 wt % of bis(ethyl-3-oxobutanato)(η-1,5-cyclooctadiene)ruthenium(II) prepared by the above method instead of the bis(ethyl-3-oxobutanato)(η-1,5-cyclooctadiene)ruthenium(II) obtained in Synthesis Example 4, a film was formed in the same way as that in Example 6. As a result, a film having a metallic luster was obtained. This film had a thickness of 0.015 μm.

Upon measuring the ESCA spectrum of this film, peaks attributable to the $Ru_{3d}$ orbital were observed at 280 eV and 284 eV. No peaks from other elements were observed whatsoever, indicating that the film was metallic ruthenium. The resistivity of the ruthenium film was measured by the four-point probe method and found to be 83 μΩcm. The film had a film density of 10.6 g/cm³. The adhesion to the substrate of the ruthenium film that has been formed here was evaluated by the crosscut tape method, from which no delamination between the substrate and the ruthenium film was observed whatsoever. The results are shown in Table 1.

Comparative Example 1

(1) Formation of Ruthenium Film (Cyclohexadienyl)ruthenium tricarbonyl was measured out in an amount of 0.05 g into a quartz boat-type vessel within a nitrogen atmosphere, and set in a quartz reactor. A silicon wafer with a thermal oxide film was placed near the downstream side of the gas stream within the reactor and, at room temperature, nitrogen gas (hydrogen gas content; 3 vol %) was passed through the reactor at a flow rate of 300 mL/min for 20 minutes. The nitrogen gas within the reactor (hydrogen gas content; 3 vol %) was then passed through the reactor at a flow rate of 100 mL/min and the interior of the system was depressurized to 13 Pa, following which the reactor was heated at 120° C. for 5 minutes. A mist was generated from the boat-type vessel, and deposits on the quartz substrate that had been placed nearby were observed. After mist formation had ended, depressurization was stopped and nitrogen gas was introduced into the system to restore the pressure. Next, at a pressure of 101.3 kPa, nitrogen gas (hydrogen gas content: 3 vol %) was passed through at a flow rate of 200 mL/min, the reactor temperature was raised to 400° C., and the system was held in this state for one hour, whereupon a film having a metallic luster was obtained on the substrate. The various properties of the resulting metallic ruthenium film were evaluated in the same way as those in Example 1. The results are shown in Table 1.

(2) Storage Stability Test

To ascertain the storage stability, deterioration upon exposure to heat was investigated by carrying out accelerated testing under applied heat. One gram of (cyclohexadienyl) ruthenium tricarbonyl was placed in a closed pressure vessel made of stainless steel and having a 50 mL capacity, the vessel was sealed under a nitrogen atmosphere and the interior of the system was depressurized to 13 Pa, following which the overall vessel was stored under heating at 110° C.

After one month, the (cyclohexadienyl)ruthenium tricarbonyl which was originally an orange solid had turned black. The vessel was then returned to room temperature and the vessel interior was flushed with dry nitrogen, following which film formation was carried out by the same procedure as that in (1) described above, but a film could not be obtained on the substrate. Hence, (cyclohexadienyl)ruthenium tricarbonyl incurred thermal deterioration in the heating test, and made film formation impossible.

(3) Test of Vaporization Characteristics

To check the vaporization characteristics, aside from using 1 g of (cyclohexadienyl)ruthenium tricarbonyl instead of 1 g of bis(methyl-3-oxo-4,4,4-trifluorobutanato)(η-1,5-cyclooctadiene)ruthenium(II), the amount of vaporization was measured in the same way as in Example 1. The results are shown in Table 1.

Comparative Example 2

(1) Formation of Ruthenium Film

The bis(2,4-pentanedionato)(η-1,5-cyclooctadiene)ruthenium(II) obtained in Synthesis Example 6 was measured out in an amount of 0.05 g into a quartz boat-type vessel within a nitrogen atmosphere, and set in a quartz reactor. A silicon wafer with a thermal oxide film was placed near the downstream side of the gas stream within the reactor and, at room temperature, nitrogen gas (hydrogen gas content; 3 vol %) was passed through the reactor at a flow rate of 300 mL/min for 20 minutes. The nitrogen gas within the reactor (hydrogen gas content; 3 vol %) was then passed through the reactor at a flow rate of 100 mL/min, and the interior of the system was depressurized to 13 Pa, following which the reactor was heated at 180° C. for 5 minutes. A mist was generated from the boat-type vessel, and deposits on the quartz substrate that had been placed nearby were observed. After mist formation had ended, depressurization was stopped and nitrogen gas was introduced into the system to restore the pressure. Next, at a pressure of 101.3 kPa, nitrogen gas (hydrogen gas content; 3 vol %) was passed through at a flow rate of 200 mL/min, the reactor temperature was raised to 400° C., and the system was held in this state for one hour, whereupon a film having a metallic luster was obtained on the substrate. The various properties of the resulting metallic ruthenium film were evaluated in the same way as those in Example 1. The results are shown in Table 1.

(2) Test of Vaporization Characteristics

To confirm the vaporization characteristics, aside from using 1 g of bis(2,4-pentanedionato)(η-1,5-cyclooctadiene)ruthenium(II) instead of 1 g of bis(methyl-3-oxo-4,4,4-trifluorobutanato)(η-1,5-cyclooctadiene)ruthenium(II), the amount of vaporization was measured in the same way as that in Example 1. The results are shown in Table 1.

TABLE 1

| | Vaporization characteristics | Characteristics of film formation | | | | | |
| --- | --- | --- | --- | --- | --- | --- | --- |
| | Amount of vaporization (g) | Storage stability | | Carrier gas | Film | | |
| | | Storage temperature and period | Change in appearance | | thickness (μm) | Resistivity (μΩ) | Film density (g/cm³) | Adhesiveness |
| Example 1 | 0.85 | — | — | Nitrogen gas (hydrogen gas content: 3 vol %) | 0.05 | 48 | 11.7 | ○ |
| | | — | — | Hydrogen gas (100 vol %) | 0.05 | 27 | 12.1 | ○ |
| | | 110° C.; after 2 weeks | Not changed | Nitrogen gas (hydrogen gas content: 3 vol %) | 0.05 | 48 | 11.7 | ○ |
| | | 110° C.; after 1 month | Not changed | Nitrogen gas (hydrogen gas content: 3 vol %) | 0.04 | 75 | 10.8 | ○ |
| Example 2 | 0.75 | — | — | Nitrogen gas (hydrogen gas content: 3 vol %) | 0.04 | 44 | 11.7 | ○ |
| | | — | — | Hydrogen gas (100 vol %) | 0.04 | 24 | 12.1 | ○ |
| | | 110° C.; after 2 weeks | Not changed | Nitrogen gas (hydrogen gas content: 3 vol %) | 0.04 | 44 | 11.7 | ○ |
| | | 110° C.; after 1 month | Not changed | Nitrogen gas (hydrogen gas content: 3 vol %) | 0.045 | 62 | 11.1 | ○ |
| Example 3 | 0.80 | — | — | Nitrogen gas (hydrogen gas content: 3 vol %) | 0.065 | 117 | 11.4 | ○ |
| | | — | — | Hydrogen gas (100 vol %) | 0.06 | 63 | 12.0 | ○ |
| | | 110° C.; after 2 weeks | Not changed | Nitrogen gas (hydrogen gas content: 3 vol %) | 0.065 | 117 | 11.4 | ○ |
| | | 110° C.; after 1 month | Not changed | Nitrogen gas (hydrogen gas content: 3 vol %) | 0.055 | 128 | 10.7 | ○ |
| Example 4 | 0.92 | — | — | Nitrogen gas (hydrogen gas content: 3 vol %) | 0.05 | 58 | 12.0 | ○ |
| | | — | — | Hydrogen gas (100 vol %) | 0.04 | 31 | 12.1 | ○ |
| | | 110° C.; after 2 weeks | — | Nitrogen gas (hydrogen gas content: 3 vol %) | — | — | — | — |
| | | 110° C.; after 1 month | Not changed | Nitrogen gas (hydrogen gas content: 3 vol %) | 0.05 | 58 | 12.0 | ○ |
| Example 5 | 0.89 | — | — | Nitrogen gas (hydrogen gas content: 3 vol %) | 0.04 | 60 | 11.9 | ○ |
| | | — | — | Hydrogen gas (100 vol %) | 0.04 | 33 | 12.1 | ○ |
| | | 110° C.; after 2 weeks | — | Nitrogen gas (hydrogen gas content: 3 vol %) | — | — | — | — |
| | | 110° C.; after 1 month | Not changed | Nitrogen gas (hydrogen gas content: 3 vol %) | 0.04 | 60 | 11.9 | ○ |
| Comparative Example 1 | 0.87 | — | — | Nitrogen gas (hydrogen gas content: 3 vol %) | 0.04 | 78 | 11.6 | ○ |
| | | 110° C.; after 2 weeks | — | Nitrogen gas (hydrogen gas content: 3 vol %) | — | — | — | — |
| | | 110° C.; after 1 month | Changed to black | Nitrogen gas (hydrogen gas content: 3 vol %) | Impossible to form a film | | | |
| Comparative Example 2 | 0.72 | — | — | Nitrogen gas (hydrogen gas content: 3 vol %) | 0.04 | 61 | 11.9 | ○ |
| | | 110° C.; after 2 weeks | — | Nitrogen gas (hydrogen gas content: 3 vol %) | — | — | — | — |
| | | 110° C.; after 1 month | — | Nitrogen gas (hydrogen gas content: 3 vol %) | — | — | — | — |
| Example 6 | — | — | — | — | 0.042 | 121 | 9.4 | ○ |
| Example 7 | — | — | — | — | 0.015 | 83 | 10.6 | ○ |

As is apparent from Table 1, the ruthenium film-forming materials according to the invention (Examples 1 to 5) had excellent vaporization characteristics, making these ruthenium film-forming materials easy to supply onto a base, in addition to which these materials also had an excellent storage stability at high temperature. By contrast, the ruthenium film-forming material of Comparative Example 1 had excellent vaporization characteristics, but had a poor storage stability at high temperatures. The ruthenium film-forming material of Comparative Example 2 lacked the chemical structure of formula (1) stipulated in the present invention. As a result, it had poor vaporization properties compared with the ruthenium film-forming material of Example 3 whose chemical structure was similar to that in Comparative Example 2.

The invention claimed is:

1. A ruthenium film-forming method, comprising:
   (1) coating onto a base by any one of spincoating, roll coating, curtain coating, dip coating, spraying and a droplet jetting process a ruthenium film-forming material comprising a compound represented by formula (1):

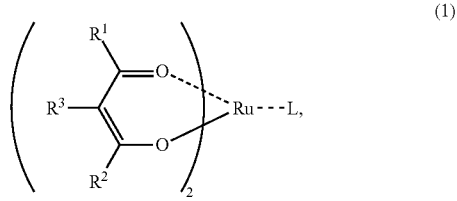

(1)

wherein:
   $R^1$ is independently a hydrogen atom, a halogen atom, a hydrocarbon group having 1 to 4 carbon atoms or a halogenated hydrocarbon group having 1 to 4 carbon atoms;
   $R^2$ is independently a halogenated hydrocarbon group having 1 to 4 carbon atoms, an alkoxy group having 1 to 4 carbon atoms or a halogenated alkoxy group having 1 to 4 carbon atoms, with the proviso that $R^1$ and $R^2$ are mutually differing groups;
   $R^3$ is independently a hydrogen atom or a hydrocarbon group having 1 to 4 carbon atoms; and
   L is an unsaturated hydrocarbon compound having 4 to 10 carbon atoms and having at least two double bonds; and
   (2) subjecting the ruthenium film-forming material on the base to heat treatment, light treatment, or both.

2. The method of claim 1, wherein $R^1$ is a hydrocarbon group having 1 to 4 carbon atoms and $R^2$ is an alkoxy group having 1 to 4 carbon atoms.

3. The method of claim 1, wherein the ruthenium film-forming material is coated onto the base by spincoating.

4. The method of claim 1, wherein the ruthenium film-forming material is coated onto the base by roll coating.

5. The method of claim 1, wherein the ruthenium film-forming material is coated onto the base by curtain coating.

6. The method of claim 1, wherein the ruthenium film-forming material is coated onto the base by dip coating.

7. The method of claim 1, wherein the ruthenium film-forming material is coated onto the base by spraying.

8. The method of claim 1, wherein the ruthenium film-forming material is coated onto the base by a droplet jetting process.

9. The method of claim 1, wherein the ruthenium film-forming material on the base is subjected to heat treatment.

10. The method of claim 1, wherein the ruthenium film-forming material on the base is subjected to light treatment.

11. The method of claim 1, wherein the ruthenium film-forming material on the base is subjected to heat treatment and light treatment.

* * * * *